US006117423A

United States Patent [19]
Berg

[11] Patent Number: 6,117,423
[45] Date of Patent: *Sep. 12, 2000

[54] HIGHLY PURIFIED SPECIES OF HUMAN LEUKOCYTE INTERFERON

[75] Inventor: Kurt Frimann Berg, Risskov, Denmark

[73] Assignee: Schering Corporation, Madison, N.J.

[*] Notice: This patent is subject to a terminal disclaimer.

[21] Appl. No.: 08/452,626

[22] Filed: May 25, 1995

Related U.S. Application Data

[63] Continuation of application No. 08/243,422, May 16, 1994, abandoned, which is a continuation of application No. 08/015,661, Feb. 19, 1993, abandoned, which is a continuation of application No. 07/752,884, Aug. 26, 1991, abandoned, which is a continuation of application No. 07/351,287, May 4, 1989, abandoned, which is a continuation of application No. 06/810,531, Dec. 17, 1985, abandoned, which is a continuation of application No. 06/506,754, Jun. 22, 1983, abandoned, which is a continuation of application No. 06/141,897, Apr. 21, 1980, abandoned, which is a continuation-in-part of application No. 06/045,962, Jun. 6, 1979, abandoned.

[30] Foreign Application Priority Data

| Apr. 20, 1979 | [DK] | Denmark | 1645/79 |
| Feb. 22, 1980 | [DK] | Denmark | 0791/80 |
| Apr. 2, 1980 | [DK] | Denmark | 1484/80 |

[51] Int. Cl.[7] .......................... A61K 38/21; C07K 14/56; C07K 16/24
[52] U.S. Cl. ................. 424/85.7; 424/85.4; 530/351; 530/413
[58] Field of Search ................... 530/351, 413; 424/85.4, 85.7

[56] References Cited

U.S. PATENT DOCUMENTS

| 3,998,947 | 12/1976 | D'Hinterland et al. . | |
| 4,132,769 | 1/1979 | Osther . | |
| 4,168,261 | 9/1979 | Edy . | |
| 4,172,071 | 10/1979 | De Maeyer et al. . | |
| 4,198,479 | 4/1980 | Tytell et al. | 435/70.5 |
| 4,241,174 | 12/1980 | Familletti et al. . | |
| 4,273,703 | 6/1981 | Osther et al. . | |
| 4,289,689 | 9/1981 | Friesen et al. | 530/351 |
| 4,289,690 | 9/1981 | Pestka et al. | 530/351 |
| 4,423,147 | 12/1983 | Secher et al. . | |
| 4,503,305 | 3/1985 | Pestka et al. . | |
| B1 4,503,035 | 3/1996 | Pestka et al. | 424/85.7 |

FOREIGN PATENT DOCUMENTS

| 1579515 | 11/1980 | United Kingdom . |
| 1579515 | 11/1981 | United Kingdom . |
| 1601744 | 11/1981 | United Kingdom . |

OTHER PUBLICATIONS

Knight, E., Proc. Nat. Acad. Sci, vol. 73, pp. 520–523, 1976.
Berthold, W., et al., J. Biol. Chem., vol. 253, pp. 5206–5212, 1978.

(List continued on next page.)

*Primary Examiner*—David L. Fitzgerald
*Attorney, Agent, or Firm*—Lerner David Littenberg Krumholz & Mentlik, LLP

[57] ABSTRACT

Disclosed is purified human leukocyte interferon, including human leukocyte interferon obtained from Namalva cells ("Namalva interferon") which, for the first time, is shown to contain a mixture of six proteins having the molecular weights of 18,400±200 daltons, 20,000±200 daltons, 20,300–20,400±200 daltons, 19,500±200, 21,300±200 daltons, and 23,400±200 daltons, as determined by SDS PAGE. Crude human leukocyte or Namalva interferon was purified using a combination of gel filtration and tandem affinity chromatography which combines ligand affinity chromatography and antibody affinity chromatography. Also disclosed are immunogenic compositions containing the purified interferon, and their use to prepare monospecific antibodies such as monoclonal antibodies which bind at least one species of the interferons. The antibodies may be used in affinity chromatography techniques to obtain highly purified human leukocyte interferons obtained from various human cells including Namalva cells.

102 Claims, 10 Drawing Sheets

OTHER PUBLICATIONS

Torma, E., and Paucker, K., J. Biol. Chem., vol. 254, pp. 4810–4816, 1976.

Rubinstein, M., et al., Proc. Natl. Acad. Sci, vol. 76, pp. 640–644, 1979.

Bridgen et al., J. Biol. Chem., vol. 252, pp. 6585–6587, 1977.

Chemical Abstracts, vol. 91, p. 461, Abst. No. 1911069, 1979.

A. Furth, "Review: Removing Unbound Detergent from Hydrophobic Proteins", *Analytical Biochemistry*, 109, pp. 207–215, (1980).

Berthold, Wolfgang et al., "Purification and in Vitro Labeling of Interferon from a Human Fibroblastoid Cell Line", *The Journal of Biological Chemistry*, 253, pp. 5206–5212, (1978).

Bollin E. et al., "The Interaction of Mammalian Interferons with Immobilized Cibacron Blue F3GA: Modulation of Binding Strength", *Preparative Biochemistry*, 8, pp. 259–274 (1978).

Bridgen, P.J. et al., "Human Lymphoblastoid Interferon, Large Scale Production and Partial Purification," *J. Biol. Chem.*, 252, pp. 6585–6587 (Oct. 1977).

Burke D.C., "The Status of Interferon", *Scientific American*, 236, pp. 42–44 (1977).

C. A. Ogburn, K. Berg, K. Paucker., "Purification of Mouse Interferon by Affinity Chromatography on Anti–interferon Globulin–Sepharose", *J. Immunol*, 111, pp. 1206–1218 (1973).

C. Anfinsen, et al., "Partial Purification of Human Interferon by Affinity Chromatography", *Proc. Nat. Acad. Sci.*, 71, pp. 3139–3142, (Aug. 1974).

CA 85:141129r, Torma, E. et al., "Purification and characterization of human leukocyte interferon components", *J. Biol. Chem.*, 251, pp. 4810–4816 (1976).

CA 87:150017w, P. Bridgen et al. "Human lymphoblastoid interferon", *J. Biol. Chem.*, 242, pp. 6585–6587 (1977).

Chadha, K.C. et al., "Molecular Size Heterogeneity of Human Leukocyte Interferon," *Biochemistry* 17, pp. 196–200 (1978).

*Chemical Abstracts*, 89:40691v, 5, (Jul. 31, 1978).

*Chemical Abstracts*, vol. 91, issued 1979, reference 209057X, Columbus, Ohio.

*Chemical Abstracts*, vol. 91, issued 1979, reference 138673g, Columbus, Ohio.

*Chemical Abstracts*, vol. 91, issued 1979, reference 209209y, Columbus, Ohio.

*Chemical Abstracts*, 86:67745r No. 11, (Mar. 14, 1977).

*Chemical Abstracts*, 90:166337y, No. 21, (May 21, 1979).

*Chemical Abstracts*, 90:202028, 25, (Jun. 18, 1979).

*Chemical Abstracts*, 91:191106a,91, p. 461 (1979).

Cantell, K., et al., "Human Leukocyte Interferon: Production, Purification, Stability, and Animal Experiments", *The Production and Use of Interferon for the Treatment and Prevention of Human Virus Infections*, Proceedings of a Tissue Culture Association Workshop, (May 1973), pp. 35–38.

Davey, M.W. et al., "Hydrophobic Interaction of Human, Mouse, and Rabbit Interferons with Immobilized Hydrocarbons," *J. Biol. Chem. 251*, pp. 7620–7625 (1976).

DeMaeyer, J. et al., "Purification of Mouse Interferon by Sequential Affinity Chromatography on poly(U) and Antibody–agarose columns," *Nature*, 271, pp. 622–625 (1978).

E. A. Havell et al., "Two antigenically distinct species of human interferon", *Proc. Natl. Acad. Sci. USA,* 72, pp. 2185–2187 (1975).

E. Havell, "Isolation of a Subspecies of Murine Interferon Antigenically Related to Human Leukocyte Interferon", *Virology*, 92, pp. 324–330, (1979).

E. Knight, Jr. "Interferon: Purification and initial characterization from human diploid cells", *Proc. Nat. Acad. Sci., USA,* 73, pp. 520–523, (Feb. 1976).

F. Hanaoka et al., "Recovery of Functional Proteins from Sodium Dodecyl Sulfate–Polyacrylamide Gels", *Anal. Biochem,* 99, pp. 170–174 (1979).

G. Bodo, "Production and Purification of Human Limphoblastoid interferon," Proc Symposium on Preparation, Standardization & Clinical Use of Interferon, *Yugoslav Academy of Sciences & Arts,* Zagreb, Yugoslavia pp. 49–57 (1977).

Hayes T.G. et al., "Le Interferon production by human fibroblasts", *Virology,* 98, pp. 351–363 (1979).

I. Heron, et al., "Enhanced expression of B2–Microglobulin and HLA antigens on human lymphoid cells by interferon", *Proc. Natl. Acad. Sci. USA,* 75, pp. 6215–6219 (Dec. 1978).

I. Heron, M. Hokland, A. Miller–Larsen, K. Berg., "The effect of interferon on lymphocyte mediated effector cell functions: Selective enhancement of natural killer cells", *Cell Immunol.,* 42, pp. 183–187, (1979).

I. Heron, et al., "Effector cell involved in cell–mediated cytotoxicity to cells Infected with Herpes Simplex virus Type 1," *Infect. Immun.,* 16, pp. 48–53, (1977).

I. Heron & K. Berg., "Interferons immunoregulatoriske funktioner", *Ugeskr. Laeg.,* 51, pp. 3210–3211 (1978).

I. Heron et al., "The actions of interferon are potentiated at elevated temperature", *Nature,* 274, pp. 508–510, (Aug. 3, 1978).

I. Heron, K. Berg., "Human Leucocyte Interferon: Analysis of effect on MLC and effector cell generation," *Scand. J. Immunol,* 9, pp. 517–526 (1979).

I. Heron et al., "Regulatory effect of Interferon on T cells in vitro", *J. Immunol.,* 117, pp. 1370–1373 (1976).

I. Heron, M. Hokland, P. Hokland & K. Berg., Effects of interferon on human lymphoid cells and their function, *Annals N.Y. Acad. Sci.,* 350, pp. 112–120 (1980).

I. Stroyer Christopherson, R. Jordal, K. Osther, J. Lindenberg, P.H. Pedersen, K. Berg., "Interferon therapy in neoplastic disease. A preliminary report." *Acta Med. Scand.,* 204, pp. 471–476 (1978).

J. Erickson et al., "Purification of acid ethanol—extracted human lymphoid interferons by Blue Sepharose chromatography", *Chemical Abstracts,* 91:191106g, *Anal. Biochem.,* 98, pp. 214–218 (1979).

J. Hedrick et al., "Size and Charge Isomer Separation & Estimation of Molecular Weights of Proteins by Disc Gel Electrophoresis", *Archives of Biochem. & Biophys,* 126, pp. 155–164, (1968).

J. Lenard et al., "Rapid and Effective Removal of Sodium Dodecyl Sulfate from Proteins", *Biochem. and Biophys. Res. Comm.,* 45, pp. 662–668 (1971).

J. McGuire et al., "Gene Expression During the Development of Bacteriophage ø29 III. Analysis of Viral–Specific Protein Synthesis with Suppressible Mutants," *J. Virology,* 13, pp. 690–698, Mar. (1974).

J. Waite et al., "Spectrophotometric Measurement of doecyl Sulfate with Basic Fuchsin", *Anal. Biochem.,* 70 pp. 279–280 (1976).

Jankowski et al., "Binding of Human Interferons to Immobilized Cibacron Blue F3GA: The Nature of Molecular Interaction," *Biochemistry*, 15, pp. 5182–5187, (1976).

Jankowski, W.J. et al., "Molecular Structure of Human fibroblast and Leukocyte Interferons: Probe by Lectin– and Hydrophobic Chromatography", *J. Virology 16*, pp. 1124–1130 (1975).

K. Berg, "Sequential affinity chromatography of human leukocyte interferon", *Scand. J. Immunol*, 6, 77–86, (1977).

K. Berg et al., "Purification of human interferons by Antibody Affinity Chromatography," *Tex. Rep. Biol. Med.*, 35, pp. 187–192 (1977).

K. Berg, et al., "Production, purification & properties of human interferons," in *Interferon & Interferon Inducers, Clinical Applications*, 2, pp. 21–56, (1980).

K. Berg, et al., "The complete purification of human leukocyte interferon," Poster Paper, *Annals N.Y. Acad. Sci.*, 350, pp. 594–595 (1980).

K. Berg et al., "The complete purification of human leukocyte interferon," *Scand. J. Immunol.*, 11, pp. 489–502 (1980).

K. Berg et al., "Pure Human Leukocyte Interferon", Proceedings from the Second Int. Interferon Workshop at Sloan-–Kettering Institute in New York, (eds. M. Krim & W. Stewart II), Apr. 22–24, (1979).

K. Berg et al., "SDS–polyacrylamide gel electrophoresis of purified human leukocyte interferon & the antiviral & anticellular activities of the different interferon species",*J. Gen. Virol.*, 50, pp. 441–446, (1980).

K. Berg et al., "The complete purification of human leukocyte interferon by tandem affinity chromatography," in *Interferon: Properties & Clinical Uses* (ed. Kahn, A.; Hill, No.O.; Dorn, G.L.) Lelands Fikes Fd. Press, Dallas, USA, pp. 33–45 (1980).

K. Berg, et al., "Affinity Chromatography of Human Leukocyte and Diploid Cell Interferons on Sepharose–bound Antibodies", *J. Immunol*, 114, pp. 640–644 (1975).

K. Berg, et al., Purification of Human Interferon by Antibody Affinity Chromatography, Using Highly Absorbed Anti–interferon. *Scand. J. Immunol*, 8, pp. 429–436 (1978).

K. Fung et al. "Heterocomplexes of Human Interferon and Immunoglobulins: Formation and Properties", *Archives of Virology*, 57 pp. 133–141 (1978).

K. Paucker et al., "Purification of interferons by immune affinity–chromatography", Proceedings of the First Intersectional Congress of the International Association of Microbiological Societies, 4, pp. 76–84 (1975).

K. Weber et al., "Reversible Denaturation Of Enzymes by Sodium Dodecyl Sulfate", *Journal Biol. Chem.*, 246, pp. 4504–4509, (1971).

K. Zoon et al., "Purification & Partial Characterization of Human Lymphoblastoid Interferon", *Proc. Natl. Acad. Sci. USA*, 76, pp. 5601–5605, (1979).

Kawakita, M. et al., "Purification of Interferon from Mouse Ehrlich Ascites tumor cells," *J. Biol. Chem. 253*, pp. 598–602 (1978).

L. Henderson et al., "A Micromethod for Complete Removal of dodecyl Sulfate from Proteins by Ion–Pair Extraction", *Anal. Biochem.*, 93, pp. 153–157, (1979).

Lin et al., "Two Dimensional Gel electrophoresis of Human Leukocyte Interferon" Abstracts of Papers submitted to the 69th Annual Meeting of the American Society of Biological Chemists and 62nd Annual Meeting of the American Association of Immunologists (joint meeting) which took place in Atlanta, Georgia on (Jun. 4–8, 1978).

Morgensen, K.E., et al., "Raising Antibodies to Human Leukocyte Interferon",*Acta Path. Microbiol. Scand. Sect. B*, 83: 443–450, (1975).

M. Rubinstein et al., "Human Leukocyte Interferon: Production, Purification of Homogeneity, and Initial Characterization", *Proc. Natl. Acad. Sci. U.S.A.*, 76, 640–644 (Feb. 1979).

M. Rubinstein et al., "Human Leukocyte Interferon Purified to Homogeneity", *Science*, vol. 202, pp. 1289–1290, (Dec. 22, 1978).

O. Kapp et al., "Removal of Sodium Dodecyl Sulfate from Proteins", *Anal. Biochem.*, 91, pp. 230–235, (1978).

Paucker et al., "Antigenic Properties and Heterospecific Antiviral Activities of Human Lleukocyte Interferon Species," *Adv. Exp. Med. Biol.*, 110, pp. 75–84, (1978).

R. Stephens, "High Resolution Preparative SDS–Polyacrylamide Gel Electrophoresis: Fluorescent Visualization and Electrophoretic Elution–Concentration of Protein Bonds", *Anal. Biochem*, 65, pp. 369–379, (1975).

S. Lacks, et al., "Effect of the Composition of Sodium Dodecyl Sulfate Preparations on the Renaturation of Enzymes after Polyacrylamide Gel Electrophoresis", *Analytical Biochemistry*, 100, pp. 357–363 (1979).

S. Pahlman, "Hydrophobic Interaction Chromatography on Uncharged Sepharose Derivatives",*J. Chromatogr,* 131, pp. 99–108 (1977).

Tan Y. H. et al., "The Isolation and Amino Acid/Sugar Composition of Human Fibroblastoid Interferon", *Journal of Biological Chemistry*, 254, pp. 8067–8073 (1979).

Torma, E. et al., "Purification and characterization of human leukocyte interferon components", *J. Biol. Chem.*, 252, pp. 4810–4816 (Aug. 25, 1976).

Tuszynski et al., "Removal of Sodium Dodecyl Sulfate from Proteins", *Anal. Biochem*, 67, pp. 55–65 (1975).

W. E. Stewart II, et al., "Distinct Molecular Species of Human Interferons: Requirements for Stabilization & Reactivation of Human Leukocyte and Fibroblast Interferons",*J. Gen. Virol.*, 26, pp. 327–331 (1975).

W. Stewart II, E. DeClercq, P. De Somer, K. Berg, C. Ogburn, K. Paucker., "Antiviral & Non–antiviral Activity of Highly Purified Interferon", *Nature (New Biology)*, 246, pp. 141–143, (Dec. 5, 1973).

W. Stewart, "Chapter 4. Purification and Characterization of Interferons," in *Interferons and Their Actions*, A. Gottlieb editor, pp. 49–72, CRC Press, New York, (1977).

Waldrop M., "Interferon production off to good start", *Chemical Engineering News*, 57, (Aug. 13, 1979), pp. 24–28.

Wietzerbin J., et al., "Physicochemical characterization and partial purification of mouse immune interferon", *J. Gen. Virol.*, 44, pp. 773–781 (1979).

1978 Annual Report of Sloan–Kettering Institute For Cancer Research pp. 222–237 (1979).

1979 Annual Report of the Sloan–Kettering Institute For Cancer Research pp. 279–292 (1980).

Abstract 202, "78th Meeting of the American Society for Microbiology", 246, (May 1978) ("the Las Vegas Abstract").

Abstract No. 953, "Annual Meeting of the American Society of Biological Chemists" (Jun. 1978), *Fed. Proc. Fed. Am. Soc. Exp. Biol.*, 37:1441 (1978) ("the Atlanta Abstract").

Borden, E.C., "Interferons: Rationale for Clinical Trials in Neoplastic Disease," vol. 91 *Annals of Internal Medicine*, 472–79 (1979).

Converse, C.A. et al., "Membrane Protein Analysis by Two–Dimensional Immunoelectrophoresis", *Science*, 189(4201), pp. 469–472 (Aug. 8, 1975).

DeMaeyer–Guignard, J. et al., "Binding ofMouse Interferon to Polynucleotides", *Proc. Natl. Sci. USA*, 74(9):3787–3790 (Sep. 1977).

Hunkapiller et al., "Direct Microsequence analysis of Polypeptides Using an Improved sequenator, a Nonprotein Carrier (Polybrene), and High Pressure Liquid Chromatography" *Biochemistry*, 17:2124–33 (1978).

Hunkapiller et al., "New Protein Sequenator with Increased Sensitivity" *Science*, 207: 523–5 (Feb. 1980).

Irvin, "Purification and Partial Characterization of the Antiviral Protein from *Phytolacca Amwericana* Which Inhibits Eukaryotic Protein Synthesis," *Archives of Biochem and Biophys*, 169, pp. 522–528 (1975).

Johnson et al., "Inactivation of Endothin by a Humoral Compoenet," *J. Exp. Med.*, 110, pp. 731–750 (1959).

Johnson et al., "Isolation from Human Serum of an Inactivator or Bacterial Lipopolysaccharide", *Amer. Journ. of Path.*, 88, No. 3, pp. 559–574 (Sep. 1977).

Lin et al., "Characterization of the Heterogeneous Molecules of Human Interferons: Differences in the Cross–Species Antiviral Activities of Various Molecular Populations in Human Leukocyte Interferons", *J. Gen. Virol.*, 39:125–130 (1978).

Salit et al., "Human Leukocyte Interferon: Separation of Biologically Different Species by Modification of Carbohydrate Moieties", *Archives of Virology*, 63, 133–142 (Feb. 1980).

Lin, L., Presentation at Sloan–Kettering Second International Workshop on Interferons, pp. 69–76 (Apr. 23, 1979) and slides accompanying Dr. Lin's Presentation.

Stewart II et al., "Molecular Heterogeneity of Human Leukocyte Interferon: Two Populations Differing in Molecular Weights, Requirements for Renaturation, and Cross–Species", *Virology*, 67:68–73 (1975).

Stewart et al., "Abstracts of the Fourth International Congress for Virology, held at The Hague", *The Netherlands*, (Aug. 30–Sep. 6, 1978) ("the Hague Abstract").

Stewart II et al., "Elimination of Size and Charge Heterogeneities of Human Leukocyte Interferons by Chemical Cleavage", *Proc. Natl. Acad. Sci. USA*, 74(10):4200–4204 (Oct. 1977).

Stewart II et al., "Identification of the Cell Multiplication Inhibitory Factors in Interferon Preparations as Interferons", *Nature*, 262, pp. 300–302 (Jul. 1976).

Stewart II et al., "Elimination of Size and Charge Heterogeneities of Human Leukocyte Interferons by Chemical Cleavage", *Proc. Natl. Acad. Sci. USA*, 74(10):4200–4204 (1977).

Stewart, W.E., II, *The Interferon System*, (1st Ed.), Springer–Verlag Wren, New York (1979 and 1981), pp. 196–222, 292–321.

Tani et al., "Utilization of Methanol by Yeasts", *Advances in Applied Microbiology*, 24, pp. 165–186 (1978).

*Wall Street Journal*, (Dec. 26, 1979), p. 1.

Wright, Christine L. et al., "Purification of the Hexokinases by Affinity Chromatography on Sepharose–N–Aminoacylglucosamine Derivatives", *Design of Affinity Matrices From Free Solution Kinetics*, 175, pp. 125–135 (1978).

Zoon et al., "Amino Terminal Sequence of the Major Component of Human Lymphoblastoid Interferon", *Science*, 207, pp. 527–528 (Feb. 1, 1980).

David S. Secher et al., "A monoclonal antibody for large–scale purification of human leukocyte interferon", *Nature*, 285, (Jun. 1980), pp. 446–449.

Oscar H. Kapp et al., "Removal of Sodium Dodecyl Sulfate from Proteins," *Analytical Biochemistry*, 91, pp. 230–235 (1978).

Dayle A. Hager et al., "Elution of Proteins from Sodium Dodecyl Sulfate–Polyacrylamide Gels, Removal of Sodium Dodecyl Sulfate, and Renaturation of Enzymatic Activity: Results with Sigma Subunit of *Escherichia coli* RNA Polymerase, Wheat Germ DNA Topoisomerase, and other Enzymes," *Analytical Biochemistry*, 109, pp. 76–86, (1980).

Kenshi Hayashi, "A Rapid Determination of Sodium Dodecyl Sulfate with Methylene Blue", *Analytical Biochemistry*, 67, pp. 503–506, (1975).

J.L. Fox et al., "SDS Removal from Protein by Polystyrene Beads," *Analytical Biochemistry*, 87, pp. 253–256, (1978).

L.T. Lee et al., "Removal of Unbound Sodium Dodecyl Sulfate (SDS) From Proteins in Solution by Electrophoresis Through Triton X–100–Agarose," *Journal of Immunological Methods*, 19, pp. 69–75, (1978).

K. E. Mogensen et al., "Human Leukocyte Interferon: a Role for Disulphide Bonds," *Journal of General Virology*, 22, pp. 95–103, (1974).

N. Fuchsberger et al., "Production of human leukocyte interferon for clinical use under immunoelectrophoretic control," *Acta Biol. Med. Germ.*, 38, pp. 795–800, (1979).

K. Paucker et al., "Purification of Mouse Interferon by Antibody Affinity Chromatography," *Effects of Interferon on Cells, Viruses and the Immune System*, pp. 639–654 (1975).

K. Paucker, et al., "Biological Properties of Human Leukocyte Interferon Components," *Journal of General Virology*, 35, pp. 341–351, (1977).

E.A. Havell, et al., "Characteristics of Human Lymphoblastoid (Namalva) Interferon," *Journal of General Virology*, 38, pp. 51–59, (1977).

S. V. Skurkovich, et al., "Preparation of Monospecific Immunoglobulin Against Human Leukocyte Interferon," *Byull. Eksp. Biol. Med.*, 86, pp. 561–563, (1978).

B. J. Dalton et al., "Production of Antibodies to Human Interferons in Mice," *Infection and Immunity*, 19, pp. 570–574, (1978).

Zoon, K., presentation at 1978 Joint NIAID/NCI Workshop On Clinical Trials With Exogenous Interferon (1978).

Dunnick, J. and Galasso, G., "Clinical Trials With Exogenous Interferon: Summary Of A Meeting," *J. Infect. Dis.*, 139, p. 109–23 (1979).

Anfinsen et al., "The Purification Of Human Lymphoblastoid Interferon," *Abstracts of the Annual Meeting of the American Society of Microbiology*, S65, p. 250, (1979).

Zoon et al., "Purification And Partial Characterization Of Human Lymphoblastoid Interferon," *Proc. Natl. Acad. Sci. USA*, 76, pp. 5601–5605 (1979).

Lin et al., "Purification Of Human Leukocyte Interferon To Apparent Homogeneity: Criteria for Purity," *Abstracts of the Annual Meeting of the American Society of Microbiology*, 202, p. 246 (1978).

Karpetsky et al., "Ribonuclease Activity of Preparations of Human Lymphoblastoid Interferon," *J. Gen. Virol.*, 44, pp. 241–244 (1979).

Balkwill et al., "Human Lymphoblastoid Interferon Can Inhibit The Growth Of Human Breast Cancer Xenografts In Athymic (Nude) Mice," *Europ. J. Cancer*, 16, pp. 569–573 (Apr. 1980).

Vilcek et al., "Antigenic, Physicochemical, and Biologic Characterization of Human Interferons," *Ann. N.Y. Acad. Sci.*, 284, pp. 703–710 (1977).

Havell et al., "Correlation of Physicochemical and Antigenic Properties of Human Leukocyte Interferon Subspecies," *Arch. Virol.*, 55, pp. 121–129, (1977).

Lin et al., "Characterization of The Size and Charge Heterogeneities of Human Leukocyte Interferon Populations," *Arch. Virol.*, 56, pp. 269–272, (1978).

Moss, B. and Rosenblum, E., "Hydroxylapatite Chromatography of Protein–Sodium Dodecyl Sulfate Complexes," *J. Biol. Chem.*, 247, pp. 5194–5198 (1972).

Balkwill, "What Future For The Inteferons?" *New Scientist*, pp. 230–232 (Jan. 24, 1980).

Anfinsen, "Biological Synthesis of Peptide Hormones," *Polypeptide Hormones:* Proceedings of the Miles International Symposium, 12, pp. 5–9 (1980).

Zoon et al., "Human Lymphoblastoid Interferon: Purification, Amino Acid Composition and Amino–Terminal Sequence," *Ann. N.Y. Acad. Sci.*, 350, pp. 390–398 (1980).

Lee et al., "The Carbohydrate of Ovalbumin" *Arch. Biochem. Biophys.*, 95 pp. 263–270 (1961).

Cesario et al., "Relationship Between the Physicochemical Nature of Human Interferon, the cell Induced, and the Inducing Agent," *Antimicrob. Agents Chemother.*, 11 pp. 291–298 (1977).

Tovey et al., "Antiviral Activity of bovine Interferons on Primate Cells," *J. Gen. Virol.*, 36 pp. 341–344 (1977).

Huet et al., Binding of Concanavalin A to Interferon–Treated Murine Leukemia L 1210 cells (38279), *Proc. Soc. Exp. Biol. Med.*, 147 pp. 52–57 (1974).

Mikulski et al., "Large Scale Purification of Human Fibroblast Interferon", *Prep. Biochem.*, 10 pp. 103–119 (1980).

Hagar and Burgess, "Elution of Proteins From Sodium Dodecyl Sulfate–Polyacrylamide Gels, Removal of Sodium Dodecyl Sulfate, and Renaturation of Enzymatic Activity: Results with Sigma Subunit *Escherichia Coli* RNA Polymerase, Wheat Germ DNA Topoisomerase, and other Enzymes," *Anal. Biochem.*, 109, pp. 76–86 (1980).

Zaman and Verwilghen, "Quantitation of Proteins Solubilized In sodium Dodecyl Sulfate–Mercaptoethanol–Tris Electrophoresis Buffer," *Anal. Biochem.*, 100 pp. 64–69 (1979).

Inoue et al., *Chemical Abstracts*, vol. 72, reference 88461 (1970).

K. Berg, C. Ogburn, K. Paucker, K.E. Mogensen, Kari Cantell—Affinity Chromatography of Human Leukocyte and Diploid Cell Interferons on Sepharose–bound Antibodies. J. Immunol. 14, 640–644 (1975).

E.A. Havell, B. Bergman, C.A. Ogburn, K. Berg, K. Paucker, J. Vilcek—Two antigenically distinct species of human interferon. Proc. Nat. Acad. Sci. USA, 72, pp. 2185–2187 (1975).

W.E. Stewart II, P. De Somer, V.G. Edy, K. Paucker, K. Berg, C.A. Ogburn—Distinct Molecular Species of Human Interferons: Requirements for Stabilization & Reactivation of Human Leukocyte and Fibroblast Interferons, J. Gen. Virol. 26, pp. 327–331 (1975).

I. Heron, K. Berg, K. Cantell, Regulatory effect of Interferon on T cells in vitro, J. Immunol. 117, pp. 1370–1373 (1976).

I. Heron, A. Miller–Larsen, K. Berg, The effector cell involved in cell–mediated cytotoxicity of HSV–1 infected cells. Infect. Immun. 16, 48–53, (1977).

K. Paucker, C. Ogburn, K. Berg, Purification of interferons by immune affinity–chromatography, p. 76–84, (1977), in T. Hasegawa (ed). Proceedings of the First Intersectional Congress of the International Association of Microbiological Societies, vol. 4. Science Council of Japan, Tokyo.

K. Berg, R. Hamilton, R. Alacam & I. Heron (1978): Purification of human interferons, in: The Interferon System. A Current Review to 1978. Tex. Rep. Biol. Med. 35, pp. 187–192.

K. Berg, I. Heron.& R. Hamilton (1978): Purification of Human Interferon by Antibody Affinity Chromatography, Using Highly Absorbed Anti–interferon. Scand. Immunol. 8, 429–436.

I. Heron, M. Hokland, K. Berg, Enhanced expression of $\beta_2$–microglobulin and HLA antigens on human lymphoid cells by interferon. Proc. Natl. Acad. Sci. USA 75, No. 12, pp. 6215–6219.

K. Berg & I. Heron, The complete purification of human leukocyte interferon. Scand. J. Immunol. 11, pp. 489–502 (1980).

K. Berg, K. Osther & I. Heron, The complete purification of human leukocyte interferon by tandem affinity chromatography in: Interferon: Properties & Clinical Uses (ed. Kahn, A.; Hill, N.O.; Dorn, G.L.). Lelands Fikes Fd. Press, Dallas, USA, pp. 33–45 (1980).

K. Berg & Iver Heron in Methods in Enzymology, Vo. 78 Part A (ed. S. Pestka) Interferons. Antibody Affinity Chromatography of Human Leukocyte Interferon, pp. 487–499, (1981).

I. Heron & Kurt Berg in *Methods in Enzymology*, vol. 79, Part B (ed. S. Pestka). *Interferons*. Procedures for the mixed Lymphocyte reaction and cell–mediated lympholysis, pp. 484–493. (1981).

I. Heron, N. Spangsbjerg, M. Hokland & K. Berg, Effects of electrophoretically pure interferon on human lymphocyte functions. in the *Biology of the Interferon System*. Elsevier/North Holland, pp. 235–239, (1981).

P. Hokland & K. Berg, Interferon enhances the antibody–dependent cellular cytotoxicity (ADCC) of human poly–morphonuclear leukocytes. J. Immunol. 127, No. 4, pp. 1585–1588, (1981).

M. Rubinstein et al., Human Leukocyte Interferon Purified to Homogeneity, *Science,* vol. 202, pp. 1289–1290, Dec. 22, 1978.

A. Furth, Review: Removing Unbound Detergent from Hydrophobic Proteins, *Analytical Biochemistry* 109, pp. 207–215, (1980).

W. Levy, et al.,.Amino acid sequence of a human leukocyte interferon, *Proc. Nat. Acad. Sci. USA* vol. 78, No. 10, pp. 6186–6190. Oct., 1981.

M. Rubinstein, Purification & structural analysis of interferon, *Phil Trans. R. Soc. Lond.*, B299, pp. 39–50, (1982).

J. Hedrick et al., Size and Charge Isomer Separation & Estimation of Molecular Weights of Proteins by Disc Gel Electrophoresis. Archives of Biochem. & Biophys., 126, pp. 155–164, (1968).

J. McGuire et. al., Gene Expression During the Development of Bacteriophage Ø29 III. Analysis of Viral–Specific Protein Synthesis With Suppressible Mutants, J. Virology, Vo. 13, No. 3, pp. 690–698, Mar., (1974).

K. Berg et al, Human Leukocyte Interferon Comprises a Continuum of 13 Interferon Species, in, Human Lymphokines, Academic Press, pp. 397–409, (1982), Edited by A. Khan & N.O. Hill.

K. Berg, Identification, Production, & Characterization of Murine Monoclonal Antibody (LO–22) Recognizing 12 Native Species of Human Alpha Interferon, Journal of Interferon Research, 4, pp. 481–491, (1984).

K. Zoon et. al., Purification & Partial Characterization of Human Lymphoblastoid Interferon, Proc. Natl. Acad. Sci. USA, 76, No. 11, pp. 5601–5605, (1979).

T. Staehelin et al., Purification of Recombinant Human Leukocyte Interferon (IFLrA) with Monoclonal Antibodies, Methods in Enzymology 78, pp. 505–512, (1981).

R. Stephens, High Resolution Preparative SDS—Polyacrylamide Gel Electrophoresis: Fluorescent Visualization and Electrophoretic Elution—Concentration of Protein Bonds, Anal. Biochem. 65, pp. 369–379, (1975).

F. Hanaoka et. al., Recovery of Functional Proteins from Sodium Dodecyl Sulfate—Polyacrylamide Gels. Anal. Biochem. 99, pp. 170–174 (1979).

Hunkapiller et. al., Isolation of Microgram Quantities of Proteins from Polyacrylamide Gels for Amino Acid Sequence Analysis, Methods in Enzymology, vol. 91, Part 1, (Eds. Hirs & Timasheff), pp. 227–236, (1983).

K. Weber et. al., Reversible Denaturation of Enzymes by Sodium Dodecyl Sulfate, Journal Biol. Chem. 246, No. 14, pp. 4504–4509, (1971).

J. Lenard, Rapid and Effective Removal of Sodium Dodecyl Sulfate from Proteins, Biochem. and Biophys. Res. Comm. 45, No. 3, pp. 662–668 (1971).

O. Kapp et. al., Removal of Sodium Dodecyl Sulfate from Proteins, Anal. Biochem. 91, pp. 230–235, (1978).

L Henderson et. al., A Micromethod for Complete Removal of Dodecyl Sulfate from Proteins by Ion–Pair Extraction Anal. Biochem. 93, pp. 153–157, (1979).

M. Sato et. al., Therapeutic effect of human fibroblast interferon on premaligrant lesions arising in oral mucosa, Int. J. Oral. Surg. 14, pp. 184–194 (1985).

D. Bothe, A Sodium Dodecyl Sulfate—Gradient Gel Electrophoresis System that Separates Polypeptides in the Molecular Weight Range of 1500 to 100,000, Anal. Biochem. 151, pp. 49–54 (1985).

Lin et al., Abstracts of Papers submitted to the 69th Annual Meeting of the American Society of Biological Chemistsand 62nd Annual Meeting of the American Association of Immunologists (joint meeting) which took place in Atlanta, Georgia on Jun. 4–8, 1978.

Jankowski et al., The Binding of Human Interferons to Immobilized Cibacron Blue F3GA: The Nature of Molecular Interaction. Biochemistry 15, No. 23, pp. 5182–5187, 1976.

E. Hanell, Isolation of a Subspecies of Murine Interferon Antigenically Related to Human Leukocyte Interferon, Virology, 92, pp. 324–330, (1979).

CA 87:150017w, P. Bridgen et al. Human lymphoblastoid interferon. J. Biol. Chem., 242(19). 6585–7 (1977).

P. Bridgen et al.—Human lymphoblastoid interferon. Large scale production an partial purification. J. Biol. Chem., 252(19). 6585–7, (1977).

CA 85:141129r, Purification and characterization of human leukocyte interferon components. Torma, E. et al., J. Biol. Chem. 252(16), pp. 4810–4816 (1976).

Purification and characterization of human leukocyte interferon components. Torma, E. et al., J. Biol. Chem. 251(16), pp. 4810–4816 (1976).

E. Knight, Jr.—Interferon: Purification and initial characterization from human diploid cells, Proc. Nat. Acad. Sci., U.S.A., vol. 73, No. 2, pp. 520–523, Feb. 1976.

W. Berthold et. al., Purification and in Vitro Labeling of Interferon from a Human Fibroblastoid Cell Line, J. Biol. Chem., vol. 253, No. 14, pp. 5206–5212 (1978).

Chemical Abstracts, 91:191106g. J. Erickson et al.—Purification of acid ethanol—extracted human lymphoid interferons by Blue Sepharose chromatography Anal. Biochem. 98(1) pp. 214–218 (1979).

W. Stewart, Chapter 4. Purification and Characterization of Interferons, B. Purification by Anti–Interferon Affinity chromatography. In Interferon and Their Action A. Gottlieb, editor, pp. 57–59, CRC Press, New York, (1977).

C. Anifsen, et. al., Partial Purification of Human Interferon by Affinity Chromatography Proc. Nat. Acad. Sci., vol. 71, No. 8, pp. 3439–3142, Aug., 1974.

Paucker et. al., Advances in Experimental Medicine and Biology, vol. 110, Human Interferon: Production & Clinical Use, published 1978, pp. 75–84.

Bollin E. et. al., The Interaction of Mammalian Interferons with Immobilized Cibacron Blue F3GA: Modulation of Binding Strength, Preparative Biochemistry, vol. 8, No. 4, (1978).

Burke D.C.—The Status of Interferon, Scientific American, vol. 236, No. 4. pp. 42–44 (1977).

CRC Immunology and Lymphoid Cell Biology Uniscience Series: Interferons and Their Actions, Stewart William E. II Editor, published 1977. (CRC Press, Cleveland, Ohio) pp. 49–72.

Chemical Abstract, vol. 91, issued 1979, reference 138 673g, Columbus, Ohio.

Tan Y. H. et al., The Isolation and Amino Acid Sugar Composition of Human Fibroblastoid Interferon, Journal of Biological Chemistry, vol. 254, No. 16, pp. 8067–8073 (1979).

Chemical Abstract, vol. 91, issued 1979, reference 209 057X, Columbus, Ohio.

Wietzerbin J.,.et al.,Physicochemical characterization and parial purification of mouse immune interferon, J. Gen. Virol. vol. 44, No. 3, pp. 773–781 (1979).

Hayes T.G. et al., Le Interferon production by human fibroblasts, Virology vol. 98, No. 2, pp. 351–363 (1979).

J. Waite et al., Spectrophotometric Measurement of Dodecyl Sulfate with Basic Fuchin, Anal. Biochem. vol. 70, pp. 279–280 (1976).

HIGHLY PURIFIED SPECIES OF HUMAN LEUKOCYTE INTERFERON

CROSS REFERENCE TO RELATED APPLICATIONS

This is a continuation application of U.S. patent application Ser. No. 08/243,422, filed May 16, 1994, now abandoned, which is a continuation of application Ser. No. 08/015,661, filed Feb. 19, 1993, abandoned, which is a continuation of application Ser. No. 07/752,884, filed Aug. 26, 1991, abandoned, which is a continuation of application Ser. No. 07/351,287, filed May 4, 1989, abandoned, which is a continuation of application Ser. No. 06/810,531, filed Dec. 17, 1985, abandoned, which is a continuation of application Ser. No. 06/506,754, filed Jun. 22, 1983, abandoned, which is a continuation of application Ser. No. 06/141,897, filed Apr. 21, 1980, abandoned, which is a continuation-in-part of application Ser. No. 06/045,962, filed Jun. 6, 1979, abandoned.

FIELD OF THE INVENTION

The present invention relates to the purification of human interferon, to a purified form of human interferon and antibodies thereto, and to purification and preparative methods relevant thereto.

BACKGROUND OF THE INVENTION

As used herein, the term "protein" includes "glycoprotein".

Many attempts have been made to purify human interferon. The objectives of such purification attempts have included a complete characterization of the interferon species for standardization purposes. To date, none of the attempts to purify human Le form interferon have been completely successful.

SUMMARY OF THE INVENTION

This invention is based on the discovery of purification methods which permit the preparation, for the first time, of all the components of human Le form interferon protein substantially free of inactive and otherwise undesirable impurities.

The Le form of interferon is defined in a paper by E. A. Havell, B. Berman, C. A. Ogburn, K. Berg, K. Paucker, and J. Vilcek, Proc. Nat. Acad. Sci. USA, 72, 2185–2187 (1975).

According to the invention, pure human leukocyte interferon proteins have been prepared from crude human leukocyte interferon through a number of special purification steps, and the pure human leukocyte interferon has been characterized by stained protein bands in SDS PAGE (sodium dodecylsulfate polyacrylamide gradient electrophoresis).

The particular experimental conditions used for the first preparation and characterization of the pure human leukocyte interferon proteins appear from the below sections "Materials and Methods" and "Experimental Section". Some of the products and procedures involved in the preparation and characterization of the pure interferon proteins are novel per se and constitute aspects of the invention of general applicability within interferon technology and, in a broader sense, in protein purification technology. The pure human interferon proteins, and especially, pure human Le form interferon proteins, now made available and characterized according to the invention, are in themselves aspects of the invention and constitute the key to further new developments which are also aspects of the invention and which are explained and illustrated in the present specification.

In several repeated experiments, it has been established that under the SDS PAGE and staining conditions described in the section "Materials and Methods", at a total interferon load of $0.9 \times 10^6$ IFU, pure human leukocyte interferon shows essentially only two sharp stained protein bands at $18,400 \pm 200$ and $20,100 \pm 200$ Daltons, respectively, and a minor stained protein band between $20,300 \pm 200$ and $20,400 \pm 200$ Daltons. As determined by the protein determination described below, the pure human leukocyte interferon has a specific activity of about $10^9$ IFU per mg of protein; the specific activity found may vary to some extent depending upon the protein determination method employed, and the specific activity on a protein weight basis is judged to be $2 \times 10^8 – 2 \times 10^9$ IFU per mg of protein. The fact that the pure interferon shows two major distinct bands is in accordance with prior art findings using crude or partially purified interferon preparations which indicated that human leukocyte interferon comprises at least two major species. At a higher total interferon load, e.g., of $3.8 \times 10^6$ IFU, the above-mentioned SDS PAGE system has been found to be capable of showing a more differentiated protein pattern comprising six interferon protein bands, i.e. the two strongly stained bands at $18,410 \pm 200$ Daltons and $20,180 \pm 200$ Daltons, respectively, a medium-stained band at $20,420 \pm 200$ Daltons (corresponding to the above-mentioned minor stained band) and just visible protein bands at $19,500 \pm 200$ Daltons, $21,130 \pm 200$ Daltons, and $23,440 \pm 200$ Daltons, respectively. Each of the individual components in the above-mentioned bands of the SDS PAGE acrylamide gradient gel has been found to show biological interferon activities: antiviral activity, ability to neutralize only anti-human leukocyte interferon (but not anti-human fibroblast interferon), and anticellular activity, plus a variety of so-called non-viral activities, as exemplified by potentiation of Natural Killer cells, potentiation of MLC-CML, increase of HLA antigens, etc.

The complete purification of interferon proteins makes it possible, for the first time, to produce anti-interferon which is strictly specific to the active species simply by immunizing animals with the pure interferon preparation or one or more of its components. Such strictly monospecific anti-interferon is extremely useful for antibody affinity chromatography for purification of crude or partially purified interferon to obtain, in a simple and economic way, large amounts of pure interferon or highly purified interferon for clinical purposes, standardization, chemical studies, sequence studies, and as immunogen for repeated preparation of monospecific anti-interferon. It is within the scope of the present invention not only to purify human leukocyte interferon by means of the monospecific antibody raised against the pure human leukocyte interferon, but also to purify other interferon types which cross-react immunologically with the monospecific anti-interferon, e.g. "Namalva" interferon (human lymphoblastoid interferons; the Le form interferon constitutes about 85% of the biological activity of human lymphoblastoid or Namalva interferon, vide E. A. Havell, Y. K. Yip, and J. Vilcek, "Characterization of human lymphoblastoid (Namalva) interferon", J. gen. Virol., 38, 51–59, (1977)), and interferon containing the Le form obtained by cultivation of a microorganism carrying DNA coding for the production of interferon proteins (or proteins having the significant biological interferon activity determinants).

The monospecific anti-interferon is also useful for establishing in a manner known per se a genetic engineering system for production of interferon protein: In accordance with known methods within genetic engineering, the first stage is the isolation of messenger RNA from interferon-producing cells in which the interferon synthesis has been triggered by means of an interferon inducer and has reached a degree of completion of the synthesis of interferon proteins at which the immunological determinants (or parts thereof) of the interferon have been expressed, while at the same time, the interferon is still attached to the ribosomes and the messenger RNA. A high clone producing Namalva cell suspension grown in the usual way or buffy coats (or lymphocytes isolated by Ficoll technique) is preferred as the interferon-producing cells. The messenger RNA is isolated from such cells by lysing the cells in a manner known per se and passing the lysate through an antibody affinity column where the antibody bound covalently is the monospecific anti-interferon. The antibody column selectively retains not only the interferon, but also the attached messenger RNA. By known methods, such as salt elution, the messenger RNA is isolated from the eluate from the column and is, also, by known methods, treated with reverse transcriptase to obtain the corresponding DNA. Alternatively, immunoprecipitation methods (known per se), possibly combined with double immunoprecipitation techniques, may be used. In accordance with known methods within genetic engineering techniques, such DNA coding for interferon or important parts thereof is incorporated in a suitable cloning vector, preferably a mini-plasmid, and transformed into a microorganism, the culturing of which produces interferon and/or interferon derivatives released in the culturing medium, from which the interferon is obtained. The purification of such interferon obtained by cultivation of the microorganism can suitably be performed in the same manner as described above by passing the crude preparation through an antibody affinity column made by means of monospecific anti-interferon. Radiolabelled monospecific anti-interferon may be a valuable tool in the assessment of which clones of the microorganism have received the DNA and are capable of producing interferon or parts or derivatives thereof.

DETAILED DESCRIPTION OF THE INVENTION

Figure 1:
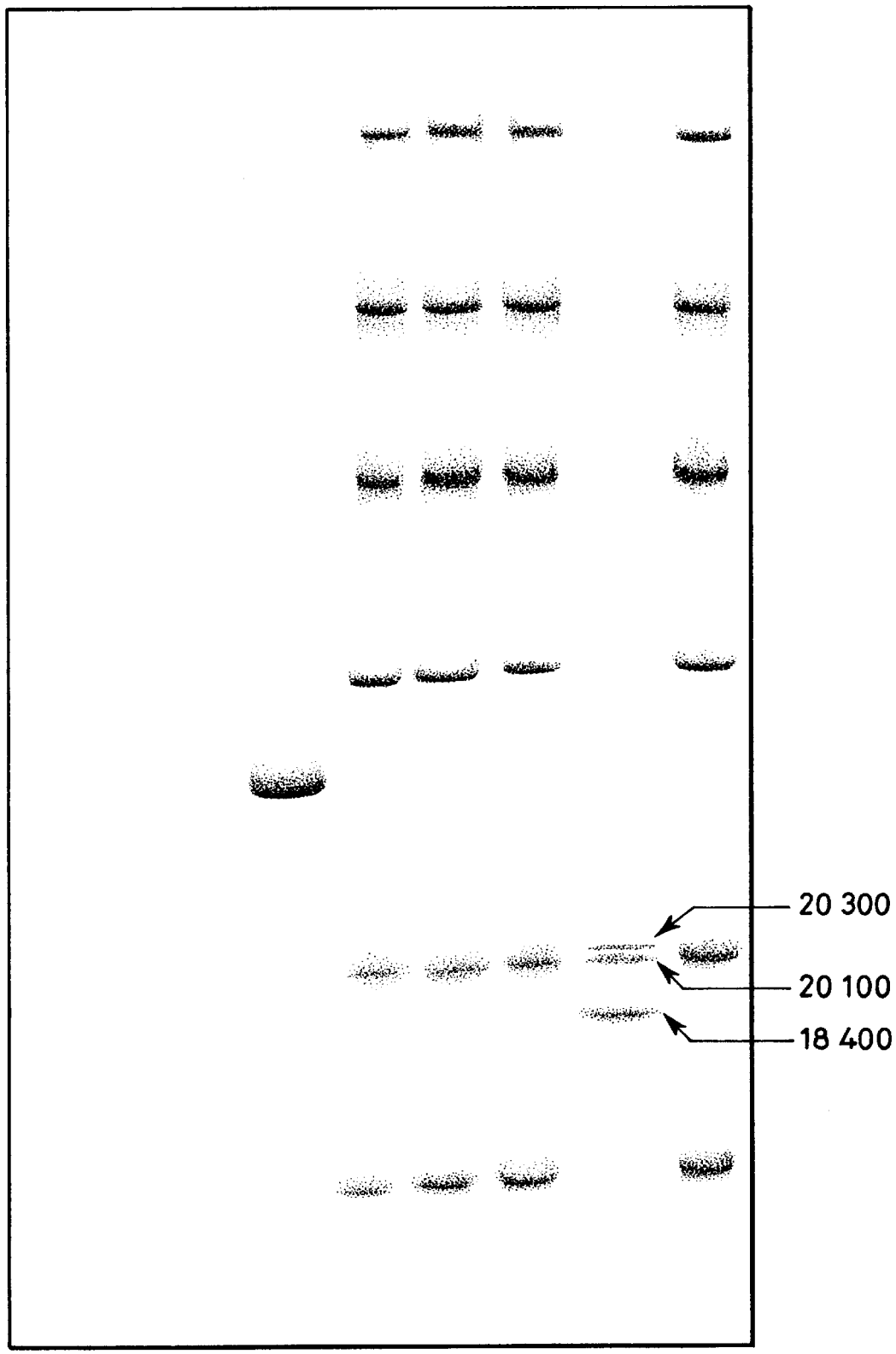
FIG. 1 is a stained SDS PAGE gradient gel slab showing five–six bands of pure human leukocyte interferon proteins obtained from an interferon load of $0.9 \times 10^6$ IFU.
Figure 2:
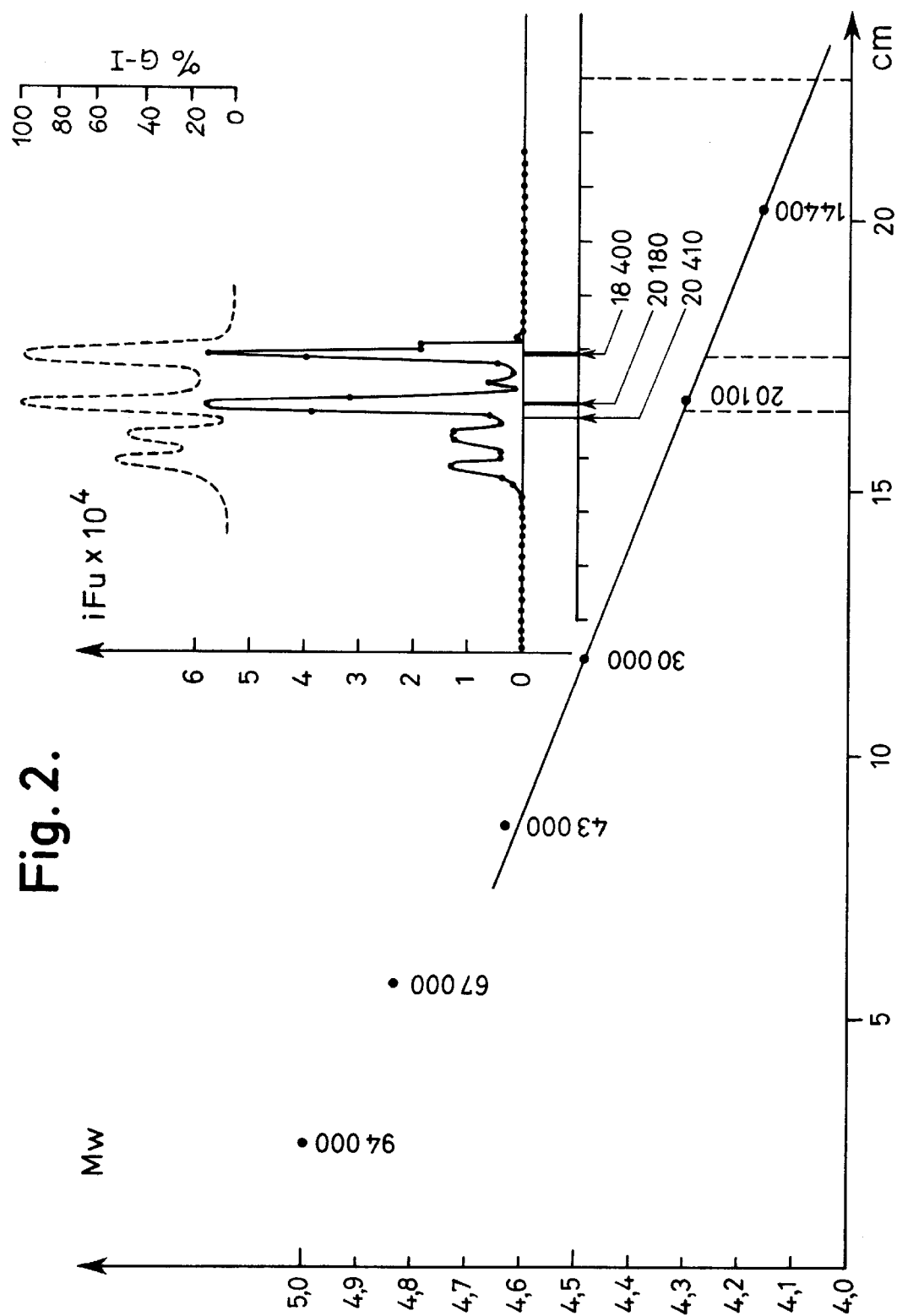
FIG. 2 is a drawing of an SDS slab from another experiment at an interferon load of $0.9 \times 10^6$ IFU showing the interferon activity associated with 5–6 bands of pure human leukocyte interferon.

At the interferon load of $0.9 \times 10^6$ IFU, the pure human leukocyte interferon proteins appear as the above-mentioned three individual protein bands in the SDS PAGE acrylamide gradient gel, together with five–six biological peaks. Whether five or six biological bands are found depends on the exact places at which the gel slice is cut. Reference is made to FIG. 1 which shows a stained SDS PAGE gradient gel slab prepared at this load as described in the section "Materials and Methods" below. Each of the protein bands has been shown to possess distinct interferon activity. Reference is made to FIG. 2 which is a drawing of an SDS slab from another experiment at the same interferon load, FIG. 2 also showing the interferon activity profile associated with the bands, determined as explained under "Materials and Methods" below. Five biological interferon peaks are seen, together with three distinct stained proteins.

Figure 3:
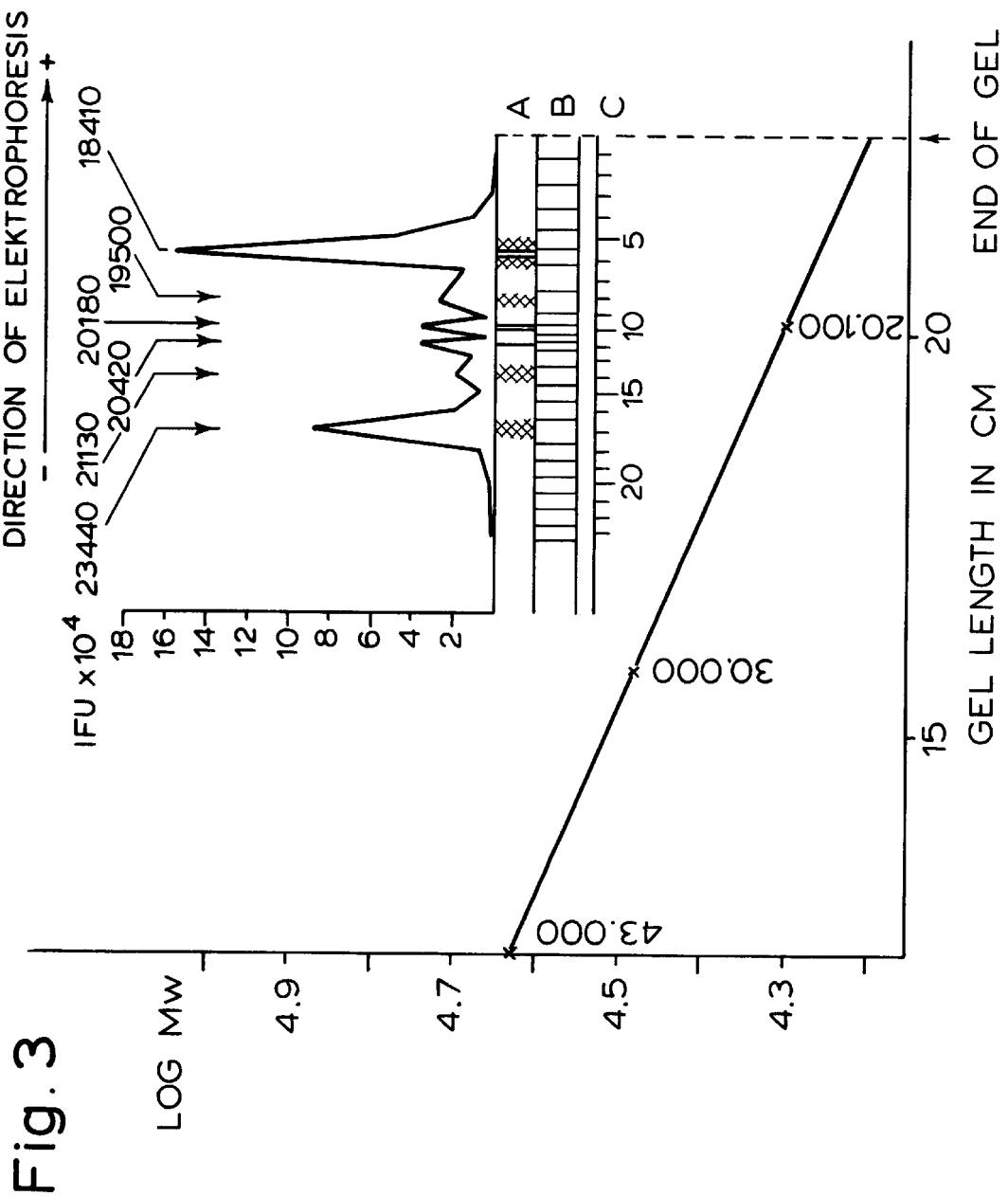
FIG. 3 is a drawing of an SDS slab at an interferon load of $0.9 \times 10^6$ IFU showing the interferon activity associated with 6 bands of pure human leukocyte interferon.

From FIG. 2 it can be seen, unambiguously, that the protein bands coincide strictly with the peaks of interferon activity. This proves that the proteins are interferon proteins. It is important to note that the interferon activity profile will, of course, depend upon the exact position of the individual slicings of the gel. In FIG. 2, the individual interferon activity of the minor band at $20,410 \pm 200$ Daltons is not so evident, but in other experiments at the same interferon load, it was shown that the minor band itself possesses interferon activity, and in experiments with a higher load, vide below, the minor band was found to be a distinct interferon subspecies. The amount of interferon activity from the SDS PAGE found in the corresponding interferon protein slices corresponds linearily with the amount of protein as assessed from the intensity of the staining of the protein bands. Thus, the unambiguous existence of the two major interferon proteins and the minor band has been demonstrated in the experiments illustrated in FIGS. 1 and 2. In experiments where the interferon load in the system was higher, the above-mentioned more detailed band pattern was demonstrated, such as illustrated in FIG. 3 (six interferon proteins together with six biological peaks determined after staining and destaining). As it is known that interferon treated with SDS will retain its immunological determinants and even expresses (or preserves) its antigenicity in a more distinct way compared to non-SDS-treated interferon (as shown by immunizations of mice with human leukocyte interferon preparations of Paucker et al. (Dalton, B. f., Ogburn, C. A., Paucker, K., Production of antibodies to human interferons in mice, Infect. Immun. 19(2), 570–574 (1978), pp 4; 25–30), preparative SDS PAGE makes it possible to not only obtain each of the components in isolated form, but also to perform immunization with the isolated components, such as illustrated in greater detail below.

Expressed with reference to specific activity, the invention relates to human interferon or species thereof having a specific activity of about $2 \times 10^8 – 2 \times 10^9$ IFU per mg protein. However, since the methodology concerning the protein determination varies considerably, the actual figure of the specific activity is of less importance compared to the clear demonstration, by SDS PAGE, of the individual species.

The pure interferon proteins of the invention are, therefore, more suitably expressed as human Le form interferon proteins which under the SDS PAGE and staining conditions defined herein at a total interferon load of $0.9 \times 10^6$ IFU show two major sharp stained protein bands having antiviral interferon activity at 18,400 and 20,100 Daltons, respectively, and a minor stained protein band having antiviral interferon activity between 20,300 and 20,400 Daltons, together with smaller peaks of antiviral interferon activity at 19,500, 21,130, and 23,440 Daltons (said Dalton molecular weights being subject to an experimental accuracy of ±200 Daltons), said SDS PAGE acrylamide gradient showing essentially no other stained protein regions; or as human Le form interferon proteins which under the SDS PAGE and staining conditions defined herein at a total interferon load of $3.8 \times 10^6$ IFU show six stained protein bands having antiviral interferon activity, viz. strong bands at 18,410 Daltons and 20,180 Daltons, respectively, a medium-strong band at 20,420 Daltons and just visible bands at 19,500 Daltons, 21,130 Daltons, and 23,440 Daltons, respectively (said Dalton molecular weights being subject to an experimental accuracy of ±200 Daltons), the peaks of antiviral interferon activity coinciding exactly with the stained protein bands, said SDS PAGE acrylamide gradient showing essentially no other stained protein regions.

It is important to note that the individual components in the above-mentioned bands of the SDS PAGE gel show biological interferon activity, ability to neutralize anti-human leukocyte interferon, and anticellular activity, etc. The invention also relates to each of the individual components represented by each of the above-mentioned individual SDS PAGE bands, as well as to any protein having the significant biological interferon activity determinant(s) possessed by the individual components, and to any protein having the significant immunological determinant(s) possessed by the individual components.

With respect to origin, the human interferon proteins of the invention may be derived from human leukocyte interferon prepared using human cells or from cultured human lymphoblastoid (Namalva) cells, or from proteins prepared by cultivation of a microorganism containing DNA coding for the interferon or an important part thereof, such as described above, but also human Le form interferons of other origin, but conforming with the above characteristics, are within the scope of the present invention.

It is well known that human Le form interferon shows a number of important therapeutic aspects in man, including antiviral and antitumor activity, and the provision of the pure human Le form interferon makes it possible to further exploit these useful properties. One aspect of the invention comprises a formulation comprising the pure human Le form interferon protein or proteins adapted for administration to human beings or animals for prophylactic, therapeutic, or immunization effect. Such a formulation may, e.g., be adapted for parenteral, intranasal, or topical administration.

A most useful formulation of the pure interferon proteins of the present invention is an aqueous solution. Pure interferon proteins in aqueous solution should be stabilized, and the choice of stabilizer will depend upon the use of the solution. When the solution is to be used for administration to human beings, e.g, parenteral administration, the stabilizer should be a physiologically acceptable stabilizer, and a suitable stabilizer is a protein or combination of proteins which is non-toxic and non-immunogenic in human beings, such as human serum proteins and fractions thereof, and human albumin. A typical preferred stabilizer is 1% human albumin. The normal concentration of pure interferon proteins in compositions for parenteral administration to human beings will be in the range corresponding to 1–20 million IFU per ml, and a normal daily dose will be 3 to 10 million, e.g. 5 to 10, million IFU totally, preferably administered once or twice a day by intramuscular injection. When preparing solutions of pure interferon for administration to human beings, normal pharmaceutical precautions which are customarily taken in connection with the preparation of parenteral compositions, will also be observed, such as precautions to ensure sterility and freedom from pyrogenicity.

When the stabilized formulation of the invention is an aqueous solution of pure human Le form interferon protein (s) to be used for immunization of animals for the preparation of monospecific anti-interferon, stabilization with SDS (sodium dodecylsulfate) to form an SDS complex of the human Le form interferon protein(s) is a preferred stabilization in view of the above-mentioned fact that SDS increases the antigenicity and/or stability of interferon. As explained in greater detail below, the pure interferon-SDS combination or complex may be formed simply by adding SDS to the aqueous pure interferon proteins, preferably in a concentration of about 0.1% by weight, calculated on the solution, at pH 7.2. The SDS complex of the human Le form interferon protein or proteins constitutes, in itself, a valuable aspect of the present invention because of the stability thereof, and a most interesting form of such complex, well suited for storage and transport (suitably at low temperature, e.g., at a temperature of at the most 4° C. or preferably −20° C., is when isolated in solid form such as described below.) The use of other stabilizers of the detergent type for this purpose is within the scope of the present invention. A further preferred form of the pure human Le form interferon proteins is a form in which they are bound to Cibacron Blue F3GA or another ligand capable of binding the interferon proteins according to the mechanism exhibited by Cibacron Blue F3GA, such as will be explained in greater detail below.

The pH of the pure interferon protein solution for immunization of animals to prepare the monospecific anti-interferon is preferably about 7.2, and a suitable buffer is PBS (phosphate buffered saline).

The stabilized pure interferon protein preparation for immunization of animals may additionally comprise an adjuvant to further increase the antigenicity, and one suitable adjuvant is Freund's adjuvant.

It is also within the scope of the invention to increase and/or stabilize the antigenicity of the pure Le form interferon proteins or each member thereof by coupling to an immunogenic carrier (so as to present the pure interferon protein or proteins as a sort of "hapten") in accordance with wellknown principles. As examples of immunogenic carriers may be mentioned PPD (Purified Protein Derivative) and BCG (Bacille Calmette Guérin). However, the use of such immunogenic carriers is not presently preferred.

For immunization purposes, mouse, rabbit, goat and sheep are preferred animals, but it is also within the scope of the invention to use other animals, and as described below, pig IgG immunoglobulins show distinct advantages for certain purposes.

In principle, the immunization of animals against the pure interferon is performed in accordance with known methods for preparation of anti-interferon, such as described, for example in Acta Path. Microbiol. Scand. Section B, 83, 443–460 (1975), but the fact that the interferon proteins of the invention are pure gives rise to minor variations with respect to the concentration of the immunogen and the immunization time and intervals. Examples of immunization schedules appear from the "Experimental Section".

The bleeding of the animal and the isolation of antiserum are performed in accordance with wellknown methods.

The antibodies prepared as described above, are, apart from the trivial fact that they show a natural background characteristic of the animal immunized, substantially specific to the interferon proteins characterized by the above-mentioned SDS PAGE bands. An extremely small amount of impurities not seen as stained bands in the SDS PAGE together with the interferon protein cannot be ruled out. Such proteins which may represent small amounts corresponding to about 1–5% of the total protein content in the pure interferon protein preparation might trigger antibodies against the corresponding impurities. One way of checking such a possibility is to construct an anti-interferon column of the relevant antiserum, obtained by immunizing a rabbit with the pure interferon (that is interferon of the above-described characterization which in SDS PAGE gives the visible interferon protein bands at a load of $1-4 \times 10^6$ IFU in total). The column is constructed without any absorption at all. Crude human leukocyte interferon is loaded to the column, and a normal antibody affinity chromatography is performed, vide below.

The eluate is analyzed in an SDS PAGE (vide below), and only the interferon bands should then be seen possibly together with 1–4 other proteins (impurities). This (three proteins) was in fact seen on rabbit anti-serum with a titer of 500,000 IFU-NU/ml in a 2 ml column, loading $2-3 \times 10^6$ IFU of crude human leukocyte interferons.

The "foreign" proteins might also appear by simple spontaneous cross reaction which by chance takes place.

The above-mentioned method of checking whether particular antibodies are monospecific is believed to be novel per se and constitutes a further aspect of the present invention. This aspect is a method for checking whether a particular antibody preparation (e.g., an antiserum), is monospecific to its particular antigen, comprising constructing an antibody affinity chromatography column by means of the antibody preparation to be checked, loading a solution containing the antigen plus impurities to the column, and analyzing the eluate from the column to ascertain the presence of any protein different from the antigen. Preferably, the latter analysis is performed by SDS PAGE gradient in the same manner as discussed in connection with the present use of the method in determining the monospecificity of anti-interferon, and the occurrence of bands corresponding to at the most 4 impurity proteins in the eluate will generally be considered a satisfactory indication of monospecificity for most practical uses of the antibody preparation.

As the stained interferon protein bands in the SDS PAGE have preserved their antigenicity completely or to a considerable extent, it is also possible to use the stained interferon proteins directly cut out from an SDS PAGE as antigen preparations for immunizing immunizable animals such as rabbits. When the stained band cut out from the SDS PAGE is used for the immunization (after preparation described below), a possible cross-over reaction (or contamination from extremely small amounts of impurities) as discussed above is less likely (compared to the total eluate representing 5 interferon species). Thus, antibodies versus the individual species of interferon (primarily the two major species at about 18,400 and 20,100 Daltons) with optimum specificity may be produced according to the following protocol:

1. $1.4-5 \times 10^6$ IFU human leukocyte interferon (as CIF) is purified completely (by means of the "tandem" affinity chromatography described below) and subjected to SDS PAGE.

2. The gel is only stained for 10–15 minutes at room temperature and is partially destained for 10 minutes followed by a wash in distilled water three times, done in 1–2 minutes with 0° C. distilled water. The exact location of the protein bands is noted (for example by means of a Polaroid photo), and the two major interferon protein species are specifically removed by cutting out with a sharp knife. Each slice is minced by means of a teflon rod in 1 ml 0.01% SDS (in PBS, pH 7.2) and is thereafter injected subcutaneously into a rabbit. By following this procedure every second week, low titered antibodies against the human leukocyte interferon proteins are developed in 2–4 months. As soon as a low titer against interferon is detected, Freund's adjuvant is added to the immunogenic mixture every fourth time (every 4th to 6th week) depending on the development of the titers. This procedure is continued for 3–12 months and anti-interferon against the interferon species is developed (10,000–1,000,000 IFU-NU/ml). Thus, the term "monospecific anti-interferon" is used both in relation to anti-interferon produced by means of the pure interferon proteins as described above without the step of cutting out from SDS PAGE, and in relation to the antibodies raised against the stained interferon band or bands cut out from the SDS PAGE.

A further method for producing monospecific antibodies against interferon proteins is the so-called hybridoma technique. The hybridoma technique is a well-known method for preparing antibodies and comprises the establishment of monoclonal antibody-producing lymphocytes/myeloma hybrids (compare, for example, "Current topics in Microbiology and Immunology, Vol. 81, Lymphocyte Hybridomas, Eds. F. Melchors, M. Potter, and N. L. Warner, Springer Verlag, 1978). However, until the present invention, it was not known or obvious that it would be possible to obtain an anti-interferon-producing hybridoma cell clone. In the hybridoma technique, using, for example, mouse as the animal immunized, mice are immunized with human Le form interferon and spleen cells from the immunized mice are fused with myeloma cells, whereafter the fused hybridoma are cloned, antibody-producing clones are selected and cultured, and antibodies are obtained from the culturing medium.

Antibodies prepared by hybridoma technique in a mouse system are strictly monospecific and are therefore especially advantageous in radioimmunoassays or other similar tests.

In the hybridoma technique, one particular way of obtaining the antibody is to culture the selected clones in vivo in the animal species from which the spleen cells were derived, and harvesting antibody from the ascites fluid of the animal, and such embodiment is within the scope of the present invention.

The selection of positive hybridoma clones may be performed by the usual interferon neutralization test. However, as the usual interferon neutralization test, as a prerequisite, requires that the antigenic determinant of the interferon is located very close to the center(s) of the biological activity (within a distance of about 1 IgG molecule length), it is likely that antigenic determinants located further away from the center(s) of the biological activity/activities will not be detected by this test, and it is, hence, likely that "positive" hybridoma clones (producing antibodies against antigenic determinants on the interferon protein which are located at a distance from the biological center which is greater than the length of 1 IgG molecule) will escape detection in the test. Therefore, a more advantageous technique for testing for positive hybridoma clones is to use radio-labelled pure human Le interferon proteins of the invention in a radioimmunoassay. The radio-labelled pure human Le interferon proteins can be made by radio-labelling human Le interferon, e.g., a gel filtrate made by the gel filtration technique described below, by means of a standard radio-labelling technique such as using lactoperoxidase and iodine 135, and then purifying the interferon proteins in the manner described herein, subjecting the purified interferon proteins to SDS PAGE and eluting the radio-labelled pure interferon proteins from the SDS PAGE gel. Another method for selecting the positive hybridoma clones in a manner which will detect also such clones that are not detected in the usual interferon neutralization test comprises subjecting an amount, e.g., 500 μl, of the supernatant from each clone cultivation to immobilization on a matrix, e.g., immobilization on CNBr-activated Sepharose according to the method described in the section "Materials and Methods", applying human Le form interferon, e.g. crude human leukocyte interferon, to the resulting,, treated matrix, e.g., by mixing the resulting matrix gel suspension corresponding to each clone with the interferon and allowing the mixture to stand for a period, e.g., 1 hour at 37° C., effectively separating unbound interferon from the matrix material, e.g., by centrifugation and washing with PBS, and thereafter subjecting each matrix gel portion to elution to release any bound interferon, e.g. by mixing with elution buffer (pH 2.4) and centrifuging, and selecting the clones corresponding to the matrix gel portions from which the eluting buffer portions, in particular the last eluting buffer portions, contain interferon, as the yielding of interferon in the elution is an indication of a positive clone. The two above-mentioned advantageous methods for detecting positive hybridoma clones may be applied not only to anti-interferon-producing hybridoma clones, but with evident modifications, also to the detection of positive hybridoma clones producing antibody directed against other proteins.

Interestingly, it has been found that antibodies raised against one of the purified interferon proteins of the invention are capable of neutralizing the other purified proteins of the invention. Thus, as will become apparent, the monospecific antibodies of the invention, whether raised against a single purified interferon protein of the invention or raised against a combination of purified interferon proteins of the invention, are equally effective for purification of human Le form interferon-containing solutions.

In accordance with well known principles, the monospecific anti-interferon of the invention can be used for determination of the corresponding interferon or interferon component in biological fluids such as by radioimmunoassay or related techniques. However, as alluded to above, an interesting and important utility of the monospecific antibodies is for antibody affinity chromatography purification of interferon-containing solutions. For this purpose, the antibodies are immobilized on a matrix in a manner known per se, suitably covalently bound to a suitable antibody affinity chromatography matrix such as a cross-linked agarose such as Sepharose 4B from Pharmacia. The antibody affinity chromatography purification of interferon-containing solutions may be performed according to any of the wellknown methods, either batchwise or, preferably, using the matrix-immobilized antibody arranged in a column.

The preparation of antibody affinity column using the monospecific anti-interferon, and the operation of such columns are performed in a manner known per se. The interferon-containing solution applied on such columns may be a crude, unconcentrated interferon preparation, or it may be a concentrated or partially purified interferon preparation. The interferon preparation applied on the column may be any interferon preparation containing human Le form interferon, that is, human leukocyte interferons, human lymphoblastoid interferons (Namalva interferons), or interferon (or important parts thereof) produced by cultivation of a microorganism containing DNA coding for interferon, such as described above. The use of antibodies against partially purified human leukocyte interferon in antibody affinity chromatography for purifying Namalva interferon and leukocyte interferon has already been described (vide, e.g. Scand. J. Immunol., 8, 429–436 (1978)). However, the important improvement is that monospecific anti-interferon will retain substantially only human Le form interferon protein, the remaining proteins of the preparation passing through the column. Very small amounts of impurities due to spontaneous cross-reactivity cannot be ruled out, not even when the antibodies used are antibodies produced by hybridoma technique which must, apart from this, be expected to "produce" (react with) only pure interferon proteins.

At suitable dimensions of such antibody columns (which can be designed in accordance with wellknown principles for antibody affinity chromatography columns), the columns may be used for large scale industrial purification of interferon from a crude interferon preparation to result in pure (or highly purified) interferon proteins in the column eluate. The pure (or highly purified) interferon proteins prepared in this way are stabilized with suitable stabilizers according to the intended use thereof, such as described above.

As the interferon of the interferon preparations applied on the monospecific anti-interferon columns is present in usually very low concentrations, on a weight basis, and as as great amounts as possible of the valuable interferon are to be isolated, it is of importance to minimize any deterioration of the interferon proteins which might be caused due to the presence of proteolytic activity in any biological substance with which the interferon is contacted, and one aspect of the present invention comprises removing any proteolytic activity from any biological material with which the interferon to be purified is in contact.

One important utility of this aspect is the removal of proteolytic activity from the anti-interferon antibodies (immunoglobulins) of the invention. According to the invention, this removal is suitably performed by treating the antibodies, prior to their binding to the matrix, with matrix-immobilized enzyme inhibitor or enzyme destructor which is not harmful to immunoglobulins (or the important fragments thereof). Thus, the antibodies may be passed through a column of matrix-immobilized poly-L-lysine and/or matrix-immobilized Soyabean Trypsin inhibitor, and/or matrix-immobilized kallikrein inactivator. An example of a suitable treatment of the antibodies is passage through a column of poly-L-lysin covalently bound to cross-linked agarose such as Sepharose 4B, followed by passages through a column of Soyabean Trypsin inhibitor covalently bound to the same matrix. It has been found that this removal of proteolytic activity increases the recovery of interferon activity in antibody affinity chromatography purification of interferon-containing solutions.

The monospecific anti-interferon, when covalently bound to a matrix such as cross-linked agarose, is preferably bound to such an extent that the total amount of antibody covalently bound to the matrix corresponds to at the most 85% of the immunoglobulins used at the covalent binding stage, such as described by the present inventor in Scand. J. Immunolog., 6, 77–86 (1977). This results in the highest recovery of interferon from the column.

When the eluate from the monospecific anti-interferon affinity chromatography column is to be used for administration in human beings, it is important that it does not contain any component which might be immunogenic in man. One risk which might be associated with antibody affinity chromatography is that immunoglobulins or immunoglobulin fragments liberate from the column and become eluted together with the desired protein or proteins.

According to the invention, such immunoglobulins or fragments thereof which are immunogenic in man are removed by passage of the eluate through an antibody affinity column in which the antibodies are directed against the anti-interferon immunoglobulins and are of a kind which is non-immunogenic on parenteral administration to human beings. (Prior to the passage of the eluate through the said column, it should be adjusted to a neutral pH, e.g. by dialysis against PBS, pH 7.2).

Immunoglobulins which are non-immunogenic on parenteral administration to human beings are primate immunoglobulins, but the access to primate immunoglobulins directed against the immunoglobulins of the animal used for the preparation of the monospecific anti-interferon may be limited or completely precluded, for legal or ethical reasons. Therefore, it is important to note that pig IgG immunoglobulins have been found to be non-immunogenic in man, such as is described in U.S. Pat. No. 4,132,769. Antibodies produced in a human hybridoma system, when available, would constitute an interesting alternative.

Hence, according to the invention, the removal of any anti-interferon immunoglobulin or immunoglobulin fraction from the eluate of the anti-interferon affinity chromatography is preferably performed by passing the eluate (after adjustment of pH to neutrality) through a column of matrix-immobilized pig IgG directed against the anti-interferon immunoglobulins.

Pig IgG immunoglobulins directed against the anti-interferon immunoglobulins may be prepared in a manner known per se by immunizing a pig with immunoglobulins from the anti-interferon immunoglobulin-producing animal species, and isolating the IgG immunoglobulin fraction from the antiserum harvested from the pig, in accordance with the methods disclosed in the above-mentioned U.S. Pat. No. 4,132,769.

In a more generalized manner, this contribution according to the present invention can be expressed as a method of removing proteins which are immunogenic in man from a protein solution which is to be administered to human beings, comprising subjecting the protein solution to an antibody affinity chromatography treatment where the antibodies are immunoglobulins directed against the immunogenic proteins, the said immunoglobulins being of a kind which is non-immunogenic on parenteral administration to human beings. As will be evident from the above explanation, the non-immunogenic immunoglobulins preferred are primate immunoglobulins or pig IgG immunoglobulins.

Other general aspects of the present invention related to this contribution are the use of pig IgG immunoglobulins as the immunoglobulins in antibody affinity chromatography using matrix-immobilized antibodies, matrix-immobilized pig IgG immunoglobulins for antibody affinity chromatography, and a process of purifying protein-containing solutions for human parenteral administration by antibody affinity chromatography, using, for the antibody affinity chromatography, matrix-immobilized pig IgG immunoglobulins. These general aspects, their utility, and their practical embodiments are evident from the above explanation.

The purification stages performed according to the present invention to prepare the pure human leukocyte interferon proteins (human Le form interferon proteins) from crude human leukocyte interferon comprise concentration by precipitation of proteins with KSCN, gel filtration, ligand affinity chromatography, and antibody affinity chromatography. Although such stages are known per se in the interferon art, the particular combination thereof and the particular conditions applied in certain of the operations constitute novel features, some of which are in themselves aspects of the present invention. The particular way in which the stages are performed, and the particular combination of operations have resulted in optimal purification and concentration of the interferon, with minimum loss of interferon proteins during the sequence.

The KSCN precipitation is preferably performed by lowering the pH of the crude interferon containing a KSCN concentration of 0.5 M to pH 4.5 instead of the conventional lowering to pH 3.5. This results in a considerably lower amount of protein in the precipitate, thus facilitating the later purification steps.

The gel filtration is performed with a buffer solution containing 25% by volume of ethylene glycol and being 1 molar with respect to NaCl, incl. PBS (pH 7.2). This results in a much better resolution than when using PBS or low pH (2,4) alone, or when using urea, PBS at pH 7.2. The eluate fractions containing essentially only proteins in the 10,000–20,000 Daltons range are collected.

The ligand affinity chromatography is performed in a novel and extremely advantageous way and constitutes one important aspect of the present invention:

The said ligand affinity chromatography is performed under specified conditions on an interferon having a specific activity of at least 50,000–100.000 IFU per mg protein, using immobilized Cibacron Blue F3GA as the ligand. The use of Cibacron Blue F3GA as the ligand for affinity chromatography of interferon was known in the art, but according to the invention, it has been found that the selectivity of this ligand increases drastically when particular combinations of conditions are used: the interferon applied should have a much higher specific activity i.e. a specific activity of at least 50,000–100,000 IFU per mg protein, than in the conventional uses of this ligand type (where crude human leukocyte interferon of a specific activity of about $3-5 \times 10^3$ IFU per mg of protein is applied), and the solution in which the interferon is applied on the column should be in the pH range of 6.5–8 and should have an ionic strength which does not essentially exceed the ionic strength of a 10–100, in particular 20, mM phosphate buffer, pH 7.2. When such a relatively high specific activity of the interferon is applied, the specificity of the ligand changes, and a higher degree of selective binding of the interferon proteins to the ligand occurs. Cibacron F3GA is believed to interact with interferon proteins in a way which indicates the existence of a "dinucleotide fold" and in this interaction, it seems to have the same binding site as polyribonucleotides. It is believed that the particular advantageous properties shown by Cibacron F3GA under particular critical conditions as discussed above will also be exhibited by the other members of the class to which this ligand pertains, and the present aspect of the invention, therefore, is constituted by a method of purifying human interferon, comprising applying an aqueous solution containing human Le form interferon protein in a form having a specific activity of at least 50,000–100,000 IFU per mg of protein, the said solution being buffered to a pH of 6.5–8 and having an ionic strength substantially not exceeding the ionic strength of a 10–100, in particular 20, mM phosphate buffer, pH 7.2 solution, optionally together with a water miscible organic solvent such as ethanol in amounts of 5–80%, on a matrix-immobilized ligand capable of binding the interferon according to the mechanism exerted by Cibacron F3GA, and thereafter eluting the interferon thus bound.

Examples of materials which are matrix-immobilized Cibacron F3GA are "Blue Dextran 2000" (matrix: dextran with molecular weight 2 millions), and Blue Sepharose CL-6B. Further details concerning these and other materials and their use in the conventional interferon purification appear from Bollin et al., Preparative Biochemistry, 8(4), 259–274 (1978).

According to the invention, it is preferred to use, as the immobilized Cibacron F3GA composition, Blue Dextran 2000 coupled to Sepharose 4B (by means of CNBr-activated Sepharose 4B).

The elution of the interferon from this type of immobilized ligand has been found, according to the invention, to be extremely selective when using 0.6 M NaCl buffered to pH 7.2, and pH 7.2 is also the preferred pH of the interferon-containing solution applied.

Figure 4:
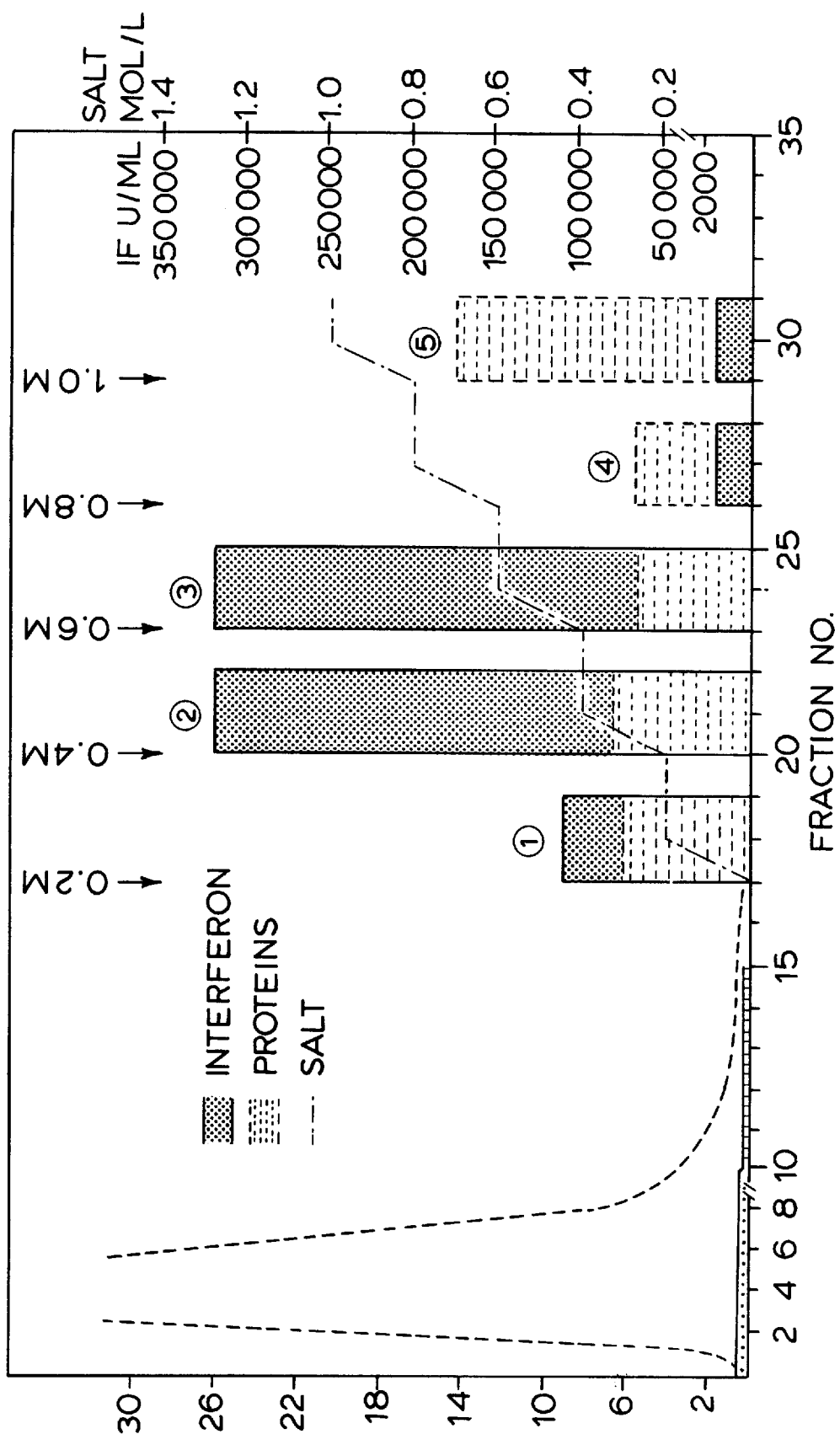
FIG. 4 illustrates the elution pattern of a Blue Dextran-Sepharose 4B column loaded with partially purified human leukocyte interferon having a specific activity of 500,000 IFU per mg protein.
Figure 4A:
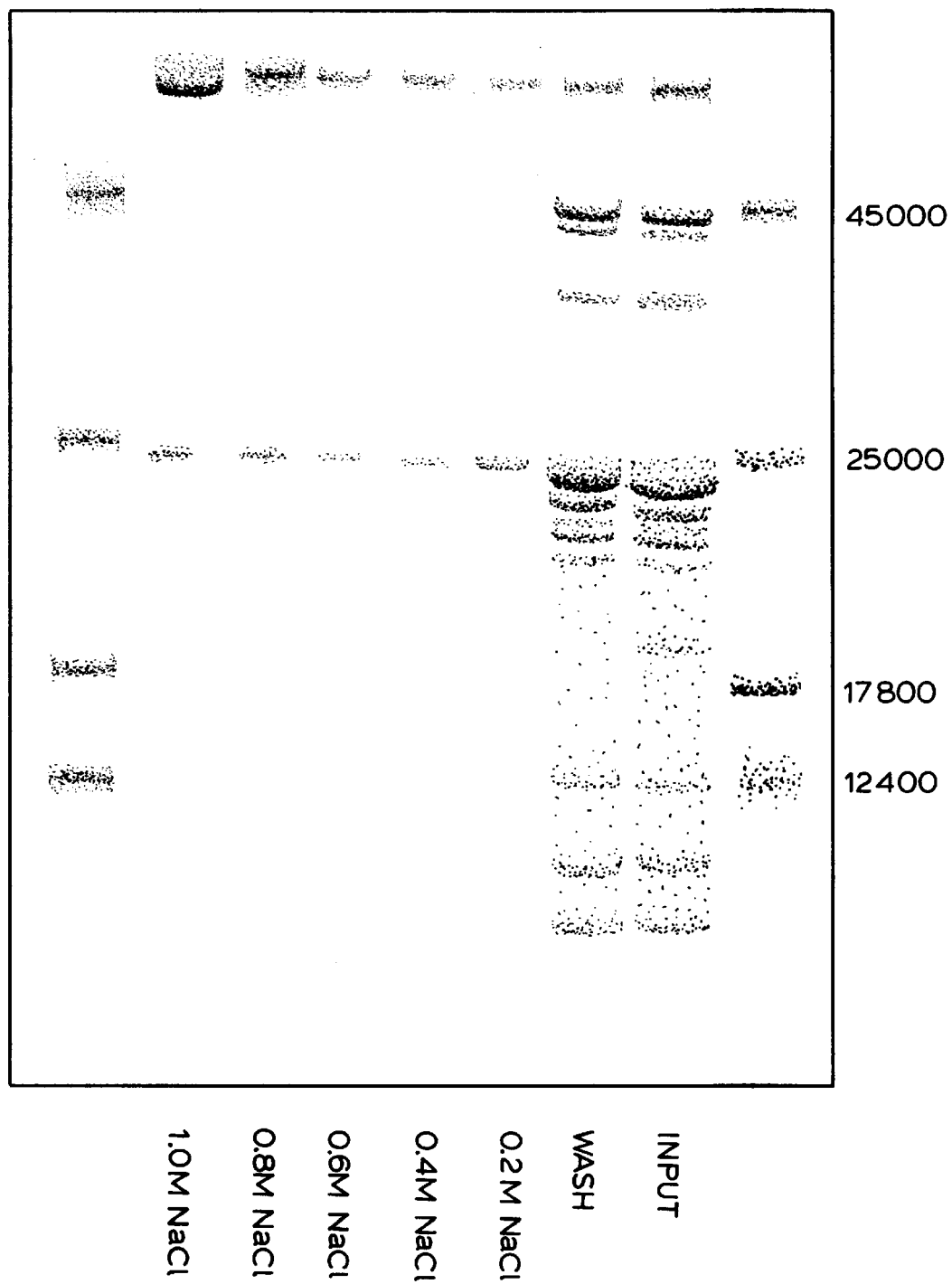
FIG. 4a is a stained SDS PAGE gradient gel slab showing the input, wash, and elutate of FIG. 4.

Reference is made to FIG. 4 which shows the elution pattern of a Blue Dextran-Sepharose 4B column loaded with partially purified human leukocyte interferon, 1 ml, specific activity 500,000 IFU per mg protein, subsequent to throughout dialysis versus 20 mM phosphate buffer (PB), pH 7.4. The size of the fractions was 5 ml, and the flow rate was 35–40 ml/h. The column was washed with 20 mM PB for 2 hours, before it was eluted stepwise with 0.2, 0.4, 0.6, 0.8, and 1.0 M NaCl in PB 7.4, respectively. The total eluate (I+II+III) contained 754,000 IFU (in 30 ml), the originally applied amount being determined to 750,000 IFU. Hence, the recovery was 100%. The specific activity of the eluate was $2.1 \times 10^7$ IFU per mg of protein. The purification factor was 42. When checking the eluates in an SDS PAGE, most of the eluted proteins (>98%) appeared above 50,000 Daltons (impurities), vide FIG. 4a which shows an SDS PAGE of the input, wash, and eluate of FIG. 4. Although, as will appear from the above, 0.6 M NaCl buffered to pH 7.2 is a most preferred eluant for the affinity column, it will also be noted that a broader concentration range is quite selective, and the invention comprises the elution with aqueous NaCl solution of a concentration of 0.5–0.7, in particular 0.5–0.65 molar and buffered to a pH of 6.5–8, or other aqueous solution buffered to a pH of 6.5–8 and having an ionic strength corresponding to such NaCl solution. The use of other eluants is also within the scope of the present invention. As examples may be mentioned salts and/or ethylene glycol in stepwise and/or gradient-wise increasing concentration up to 50%, aminoacids, artificial aminoacids, ampholines, and proteins and protein mixtures. As mentioned above, the interferon solution may be applied together with a water miscible organic solvent, such as alcohol, in particular ethanol.

The interferon which is purified by the affinity chromatography according to this aspect of the invention is typically an interferon containing human Le form interferon proteins, such as human interferons (apart from human fibroblast interferons), that is, e.g., human leukocyte interferons, human lymphoblastoid interferons and human Le form interferon proteins or important parts thereof when produced by cultivation of a microorganism clone containing DNA coding for the production of such interferon protein. (The fact that human lymphoblastoid interferon (Namalva) contains a minor proportion of interferon of fibroblast character (F form—corresponding to 15% of the biological activity) does not detract from the fact that human lymphoblastoid interferon is, with respect to its major interferon activity, a human Le form interferon in that it contains human Le form interferon proteins (corresponding to 85% of the biological activity) having determinants identical with determinants of human leukocyte interferon proteins, such as has been shown according to the present invention.)

It is preferred that the specific activity of the interferon preparation applied on the affinity column is 100,000–1,000,000, such as 200,000–1,000,000, e.g. about 500,000, e.g. 500,000–1,000,000 IFU per mg protein.

The eluate from the affinity chromatography column operated in accordance with this aspect of the invention may be an interesting product also for therapeutic use. It will often have a specific activity of at least $30 \times 10^6$ IFU per mg protein, based on the Lowry procedure using pure human albumin serum as standard, such as $30 \times 10^6 - 10^8$, e.g., $30 \times 10^6 - 70 \times 10^6$ IFU per mg protein. For administration to human beings, this preparation is subject to normal pharmaceutical precautions, such as precautions to ensure sterility and freedom from pyrogenicity. The dosage of this preparation will correspond to the dosage stated above for the pure interferon, on a total activity basis.

As explained in the "Experimental section", the eluate from the affinity chromatography column was, in the original experiments leading to the pure interferon, subjected to final purification by passage through an absorbed antibody affinity column in which the antibodies are immunoglobulins raised against partially purified human leukocyte interferon and then subjected to removal of antibodies against contaminating proteins by several passages through columns of matrix-immobilized crude human leukocyte interferon. As appears from the more detailed explanation below, the covalent binding of crude interferon to a matrix (as e.g. Sepharose 4B) destroys the immunological determinants of the interferon itself, (>98%), but apparently not the determinants of the major part of the impurities, and this means that when immunoglobulins raised against partially purified leukocyte interferon are passed (normally several times) through the column, the anti-impurities thereof will be retained on the column, while the anti-interferon will pass the column. Such absorbed anti-interferon (absorbed several times) was used in the antibody affinity chromatography stage following the affinity chromatography.

As appears from the "Experimental section", a preferred way of operating the affinity columns, that is, the Blue Dextran Sepharose column and the antibody affinity column, is to connect the two columns so that the eluate from the Blue Dextran column at the same time loads the antibody affinity column. This prevents any loss which might otherwise occur if the eluate fractions from the Blue Dextran column were handled separately.

In the final concentration of the human Le interferon proteins, a unique method of concentrating proteins by precipitation with SDS was used. This method constitutes a further aspect of the present invention and comprises precipitating SDS or a salt thereof from a solution of the protein which contains SDS, preferably in a concentration of 0.1–4 per cent by weight, in particular about 0.1 per cent by weight, to obtain a precipitate comprising a complex or complexes of SDS or a salt thereof with the protein, separating the precipitate from the solution, preferably by centrifugation at 0–4° C., and redissolving the precipitate in a smaller liquid volume. The precipitation of the SDS may suitably be obtained by either a) lowering the temperature to 0° C. for about 15 minutes or b) adding a salt, e.g., a $K^+$ salt, which forms a precipitate with SDS or with SDS-protein complexes. This method is a valuable method for concentrating aqueous solutions of pure or purified interferons, and, as indicated above, has been found to be an excellent way of concentrating human Le form interferon proteins.

The total purification sequence performed in accordance with the present invention was found to be extremely activity-preserving: From a starting amount of proteins of $7 \times 10^5$ gamma, the pure interferon isolated was less than or equal to 1 gamma, (as determined by comparison of protein bands on SDS PAGE). Yet, the overall decrease in total interferon activity from the starting batch of crude interferon to the pure interferon was only from $4 \times 10^6$ IFU to $1.85 \times 10^6$ IFU (about 50%). This emphasizes the unique character of the purification sequence and the above-mentioned critical stages thereof.

As indicated above, it has been found that the covalent binding of crude interferon to a cross-linked agarose (Sepharose) matrix can be performed under conditions which will substantially destroy the immunological determinants of the interferon itself, and this relates to another important aspect of the present invention. According to this aspect, non-anti-interferon immunoglobulins are absorbed from antiserum raised against a partially purified human interferon, by subjecting the antiserum to an absorption treatment by means of a matrix-immobilized crude concentrated human non-fibroblast interferon which has been bound covalently to the matrix in such a way that the major part of the interferon activity thereof has been destroyed. The extent to which the interferon activity has been destroyed by the binding to the matrix can be assessed using the normal interferon assay methods described in the section "Materials and Methods". It is preferred that at least 90% of the interferon activity has been destroyed, preferably at least 97 or 98% thereof, in order to avoid excessive removal of anti-interferon activity from the immunoglobulins. It has been found that when crude concentrated human leukocyte interferon is bound to cross-linked agarose ("Sepharose" (which may be CNBr-activated, epoxy-activated, or CH-activated)), the interferon activity thereof is destroyed to a large extent if the binding is performed in such a manner that at least 50% of the proteins present are bound on the matrix. Apparently, the major part of the antigenic determinants as far as the impurities are concerned survive the treatment.

The most suitable way of performing the absorption is to build up a column of the matrix-immobilized crude concentrated human interferon and pass the anti-interferon through the column. It is often preferable to pass the anti-interferon through a column of matrix-immobilized human serum prior to the passage through the column of matrix-immobilized crude concentrated human interferon, because human serum will in itself bind a considerable part of the antibodies present in the antiserum raised against partially purified human interferon. However, it has been found that a human serum alone is not capable of yielding such a high degree of purification as is possible with matrix-immobilized crude concentrated human interferon, and this is believed to be due to the fact that some of the impurities in the partially purified human interferon against which the antiserum has been raised are not normal cellular proteins, or are normal cellular proteins present in "abnormally" high concentrations in the induced cells. Therefore, according to the principles of this aspect of the invention, it was attractive to absorb antibodies to impurities from an anti-interferon serum by means of a crude interferon preparation having a relatively low concentration of interferon and a high concentration of impurities. This unique concept, combined with the finding that it was possible to destroy the interferon activity and, concomitantly, the interferon determinants, of the crude concentrated human interferon immobilized on a matrix such as cross-linked agarose, forms the basis of a most useful technique according to which the absorbed antiserum, which contains a much lower concentration of non-antiinterferon immunoglobulins, is used for antibody affinity chromatography to purify human interferons, including human leukocyte interferon and human Namalva interferon, to a high degree of purity in a simple and economic way.

In the experiments so far conducted, it appears that CH-activated cross-linked agarose (Sepharose) is the matrix on which crude concentrated human leukocyte interferon is capable of yielding the highest degree of purification of an antiserum raised against partially purified human leukocyte interferon, but that the interferon when bound to this matrix results in a somewhat higher reduction of the antiinterferon activity than when the crude concentrated human leukocyte interferon is bound to CNBr-activated Sepharose or epoxy-activated Sepharose. Therefore, a preferred way of performing the absorption is to pass the antiserum (which has preferably already been absorbed in a column with matrix-immobilized human serum) first through a column of epoxy-activated Sepharose or CNBr-activated Sepharose, and thereafter through a column of crude concentrated human leukocyte interferon bound to CH-activated Sepharose. The antiserum is passed several times through the columns until the desired purification thereof has been obtained such as can be assessed by eluting the column subsequent to passing the antiserum and determining the amount of proteins eluted. A typical procedure is to pass the antiserum 4–6 times through a column of human serum protein followed by 4–8 times through a column of human crude concentrated leukocyte interferon covalently bound to epoxy-activated Sepharose and thereafter 1–3 times through a column of the human crude concentrated leukocyte interferon bound to CH-activated Sepharose.

During these absorption procedures, the anti-interferon is obtained in the wash, and the eluate is discarded. However, the amount of protein in the eluate is indicative of the degree of purification obtained. In the final stage of purification, the degree of protein elutable from the column after the last passage of the antiserum should preferably be at the most 30 $\mu$g when the column is of a size of the order of 10–50 ml.

The degree to which the anti-interferon activity is recovered in the wash upon passage through the column is another indication of to what extent the crude concentrated human leukocyte interferon has successfully been covalently bound to the matrix in such a way that the immunological interferon determinants thereof have been destroyed. The anti-interferon should preferably pass through the column with retainment of at least 90%, preferably at least 95%, of its anti-interferon activity.

In analogy with what has been stated above, the immunoglobulins absorbed in accordance with this aspect of the invention are preferably freed of any proteolytic activity prior to being bound to the matrix. This may be obtained in the manner described above, preferably by passing the immunoglobulins through a column of matrix-immobilized enzyme inhibitor or enzyme destructor, preferably several times such as 3 times.

Another aspect of the invention is constituted by matrix-immobilized anti-interferon from which non-anti-interferon immunoglobulins have been absorbed such as described above.

A further aspect of the invention is a method of purifying human interferon by subjecting a human interferon-containing solution to antibody affinity chromatography using as antibody anti-interferon immunogobulins from which non-anti-interferon immunoglobulins have been absorbed by the method herein described, and eluting the antibody-bound interferon. In this aspect, the anti-interferon is immobilized on a suitable matrix in accordance with the general principles described further above. As appears from the experimental section, any human Le form interferon-containing solution can be purified in this manner, including human leukocyte interferon, and the Le form of human Namalva interferon. The resulting purified interferon solutions may have a very high degree of purity and are then suitably stabilized in the same way as described above for the pure or purified human leukocyte interferons prepared in accordance with other aspects of the present invention, and may be used for the same purposes as the other highly purified interferon preparations mentioned further above.

MATERIALS AND METHODS

Interferon assays were performed according to the well-known standard method (Berg K., Sequential Antibody Affinity Chromatography of Human Leukocyte Interferon, Scand. J. Immunol. 6, 77–86 (1977)) using VERO cells (monkey kidney cells) and Vesicular Stomatitis Virus (VSV) as a challenge virus. All interferon units (IFU) are expressed in international reference units (69/19 B units) (69/19 B reference was obtained from MRC, Mill Hill, U.K.)

Interferon. Crude human leukocyte interferon was produced according to the method as described by Cantell (Cantell, K., Hirvonen, S., Mogensen, K. E. and Pyhälä, L., Human leukocyte interferon: production, purification, stability and animal experiments. In: The Production and use of Interferon for the Treatment and Prevention of Human Virus Infections pp. 95–38, Waymouth, C. (ed.). Proceedings of a Tissue Culture Association Workshop held at Lake Placid, 1973 (In Vitro Monograph, volume 3), Tissue Culture Association, Rockville, Md.) using Sendai virus as interferon inducer. Partially purified interferon (PIF) with a specific activity of $5 \times 10^5$ IFU/mg protein was obtained from crude concentrated human leukocyte interferon (CIF) by ethanolic precipitation as described by Cantell, K., Hirvonen, S., Mogensen, K. E. and Pyhälä, L., loc. cit.

Crude Namalva interferon was produced substantially as described by Strander et al., Production of human lymphoblastoid interferon, J. Clin. Microbiol. 1, 116–124 (1975), using Sendai virus as interferon inducer.

Interferon neutralization for determining anti-interferon was performed in a micro-assay system in the following manner: 20,000 VERO cells per well were seeded in 100 $\mu$l medium and kept at 5% $CO_2$ in a humidified cabinet. On day 2 the medium was removed from the cells, and each well received 100 $\mu$l of a dilution (in medium) of the antiserum, containing an interferon concentration of 6–8 IFU/ml (the serum and interferon had been preincubated at 37° C. for 1 h). On day 3 the medium was removed, and all the wells received 100 $\mu$l VSV (diluted to $10^{-3.5}$ in medium). On day 4 the CPE (cytopathogenic effect) was determined, and 50% destruction was taken as the end point for the determination of the anti-interferon titer. The titers are expressed as interferon neutralization units (IFU-NU) per ml.

Non-monospecific anti-interferon against PIF was produced, according to Mogensen, K. E., Pyhälä, Liisa and Cantell, K., Acta path. microbiol. scand. Sect. B, 83, 443–450, (1975), partly in sheep, partly in rabbits. The titer of the sheep anti-interferon was 100–250,000 IFU-NU/ml. For the preparation of the rabbit anti-interferon, a rabbit was injected weekly, s.c. with PIF ($2 \times 10^5$ IFU) for more than two years. The titer of the rabbit anti-interferon was 15,000–30,000 IFU-NU/ml. All immunoglobulins were isolated by 50% ammonium sulphate precipitation, followed by a dialysis versus phosphate buffer saline (PBS), pH 7.2.

Chemicals. CNBr was from Fluka (stored at −20° C.). Sodium dodecylsulphate (SDS), specially pure for electrophorese, was purchased through British Drug House (BDH). Soyabean Trypsin Inhibitor (STI) and L-Lysine were obtained from Sigma. Sepharose 4B, CNBr-activated Sepharose 4B, CH-activated Sepharose 4B, and Epoxy-activated Sepharose 6B were all purchased from Pharmacia (Denmark).

Binding Procedures. The covalent binding of the immunoglobulins to Sepharose 4B was done as previously described by K. Berg in Scand. J. Immunolog., 6, 77–86, (1977). Only 80–85% of the immunoglobulins were deliberately bound.

Protein determinations were made by a modification of the Lowry procedure (Berg K., Sequential Antibody Affinity Chromatography of Human Leukocyte Interferon, Scand. J. Immunol., 6, 77–86 (1977)) which permitted detection of 1–2 $\mu$g/ml as the lowest level of proteins detectable (using an LKB Calculation Absorptioner Ultralab System). Crystalline bovine serum albumin was used as a standard protein. To determine the protein concentration of the purified interferon (1–5 $\mu$g in total) the following procedure was adopted: SDS was added to a final concentration of 0.1%. The lyophilized protein sample was further examined on an SDS-polyacrylamide gel electrophorese (SDS PAGE, see later), subsequent to a dialysis versus distilled water. The intensity of the stained protein bands was compared with known standards in different amounts (see later, under SDS PAGE), and the total amounts of proteins were estimated The deviations were 5–10%, with the lowest detectable level of proteins being 0.1 $\mu$g (in total). The results from this method will serve as a rough estimate, rather than as an actual measurement.

Affinity chromatographies were performed at 4° C. The gel suspensions were degassed before packed into the columns. Packing was performed by washing with 3–5 bed volumes of loading buffer, using a peristaltic pump. Samples (100 $\mu$l) for interferon titrations were taken from either pools or individual fractions and titrated on the same day or frozen in plastic tubes (−20° C.) and titrated later. The dilutions were made in medium (incl. 10% calf serum).

Antibody affinity chromatography was essentially done as described by Berg (Sequential Antibody Affinity Chromatography of Human Leukocyte Interferon, Scand. J. Immunol., 6, 77–86 (1977)). As loading buffer was used 0.1 M NaOA/0.3 M NaCl at pH 7.2 (flow rate 40 ml/h). Stepwise elution was performed with 0.1 M HOAc/0.3 M NaCl including a minute amount of citric acid (enough to keep the pH firmly at 2.4). When not operated, the column was stored at 4° C. in PBS 1 M NaCl including Penicillin Streptomycin, Gentamycin and Chloramphenicol (1% of each). Before using the column for purification purposes, it was first washed with 100 ml of loading buffer followed by 10 ml of eluting buffer and finally equilibrated with 20–30 ml of loading buffer. This washing-cycle was necessary to avoid "spontaneous" proteins, especially when working with interferon of specific activities above $10^7$ IFU/mg proteins. The plastic tubes used for collecting the interferon eluate were pre-wetted with 100 µl of 1% SDS.

SDS PAGE. The purified, concentrated interferon preparations were analyzed for polypeptides components on SDS PAGE slab gels using 20 cm long separating gels, 0.75 mm thick (Bio Rad model 221: Dual vertical slab gel electrophoresis cell) and 7–10 cm long stacking gel. Exponential gradient gels of about 9–22% polyacrylamide were prepared by mixing 11 ml 22% acrylamide solution with about 32 ml 9% solution in a simple, ice-cooled gradient-device, as described in Knight, E., Interferon: Purification and initial characterization from human diploid cells. Proc. Natn. Acad. Sci. USA 73, 520–523 (1976). The discontinuous buffer system, as described by Laenomli (Laenomli, U.K., Cleavage of Structural Proteins During Assembly of the Head of Bacteriophage T4, Nature 227, 680–685 (1970)) was used. The gel was pre-cooled for 2 h (10° C.) before starting the actual electrophorese which was performed overnight (10° C.) at constant effect (LKB power supply), starting out with 10 mA (and about 20 V). Samples to be analyzed were dissolved (or diluted) in 0.1 M Tris, HCl (pH 6.8) 2.5% SDS and 5% glucose including a tracking dye (sample buffer). The gel was stained in Comassie Blue (1.25 mg/ml in 50% methanol, 40% $H_2O$ and 10% acetic acid), without prior fixation, for 15 minutes at room temperature under constant rocking, and destained in 7% acetic acid (5% methanol). The gels were dried on paper of a good quality (for example, Whatman Chromatographic paper (17 mm)) under heat and vacuum using a gel dryer (Bio Rad, gel slab dryer, model 224). Solutions of five different molecular markers, from 0.1 µg to 10 µg of each marker per 20 µl,—Lactalbumin (14,400 Daltons); Soyabean Tripsin Inhibitor (20,100 Daltons); Carbonic Anhydrase (30,000 Daltons); Ovalbumin (43,000 Daltons); Bovine Serum Albumin (67,000 Daltons); Phosphorylase (94,000 Daltons) (obtained as an electrophoresis calibration kit (Pharmacia, Denmark))—were subjected to SDS PAGE and stained. It should be noted that molecular weights assessed in this manner are subject to experimental accuracy of about ±200 Daltons. The stained protein bands were compared with the corresponding bands obtained from a parallel SDS PAGE of a purified interferon preparation and the total concentration of interferon proteins was estimated. For obtaining a biological profile from an SDS PAGE, the part of the gel intended for interferon determination, was cut from the remainder gel and kept at 4° C. (in a humidified box) on a glass plate. The main part of the gel was stained for 15 minutes; after destaining for additionally 3–5 minutes, weak bands were clearly seen on a blue background, whereby the precise location of the protein bands corresponding to 14,000 and 30,000 Daltons could be established. The unstained part of the gel was cut, so it only contained proteins between 14,000 and 30,000 Daltons and was further subdivided in 1 mm pieces by sharp knives. The interferon from these slices was eluted with 0.5 ml 0.1 M SDS subsequent to a complete mincing by means of a teflon rod. After 5 h at room temperature (rocking) the interferon activity of the supernatant was determined. The individual fractions were frozen at −20° C. without any additives.

EXPERIMENTAL SECTION

Preparation of Pure Human Leukocyte and Lymphoblastoid Interferon Proteins

Concentration of crude human leukocyte interferon. To 3 liters of crude human leucocyte interferon was added KSCN up to a concentration of 0.5 M at pH 7.2. The pH was lowered by addition of 1N HCl to 4.5 (magnetic stirring) whereby a protein precipitate containing the interferon (and part of the impurities) was obtained. The precipitate was dissolved in 150 ml of PBS (phosphate buffered saline, pH 7.2) including 1 M NaCl and 25% by volume of ethylene glycol and dialyzed thoroughly versus 3 times 2 liters of the same buffer at 4° C. The specific activity of the crude concentrated human leukocyte interferon (HuLeCIF) was $5-10\times10^3$ IFU/mg protein. The recovery was about 98%.

Concentration of crude Namalva interferon. To 1 liter of crude Namalva interferon, with a titer of about 8000 IFU/ml, was added KSCN up to a concentration of 0.5 M at pH 7.2. The pH was lowered by addition of 1N HCl to 4.5 (magnetic stirring) whereby a protein precipitate containing the interferon (and part of the impurities) was obtained. The precipitate was dissolved in 50 ml of PBS, pH 7.2, including 1 M NaCl and 25% by volume of ethylene glycol and dialyzed thoroughly versus 3 times 2 liters of the same buffer at 4° C. The specific activity of the crude concentrated Namalva interferon (NaCIF) was $10-12\times10^3$ IFU/mg protein. The recovery was about 98%.

Gel filtration. A 100 cm long column (2.6 cm in diameter, Pharmacia K 2.6/100) was packed with Ultrogel AcA 5/4 (LKB Denmark) in PBS containing 1 M NaCl and 25% by volume of ethylene glycol at 4° C. (pH 7.2). After washing the column with 3 bed volumes of buffer, the column was stabilized. 10–15 ml of HuLeCIF (prepared as described above in 25% by volume of ethylene glycol, 1 M NaCl in PBS, pH 7.4) were loaded to the column, and the column was "eluted" with the loading buffer, the fractions being assayed for interferon activity. The interferon-containing fractions were pooled, and about 95% of the original interferon activity was recovered. The specific activity of the gelfiltered human leukocyte interferon-containing eluates was close to 1,000,000 IFU/mg protein, corresponding to a purification factor of 200. As determined by means of molecular markers, the molecular weight of the interferon corresponds to a range of 10,000–20,000 Daltons. Titrations of individual fraction revealed only one broad peak, with a maximum at 18,000 Daltons.

In the same manner as described above, 10 ml of NaCIF (prepared as described above in 25% by volume of ethylene glycol, 1M NaCl in PBS, pH 7.4) were loaded to the column, and the "elution" was performed in the same manner as described above. The recovery was about 90%. The specific activity of the gelfiltered Namalva interferon-containing eluate was close to 1,000,000 IFU/mg protein, corresponding to a purification factor of 100. As determined by means of molecular markers, the molecular weight of the interferon corresponds to a range of 10,000–20,000 Daltons. Titrations of the individual fractions revealed a broad peak, with a maximum at 18,000 Daltons.

Figure 5:
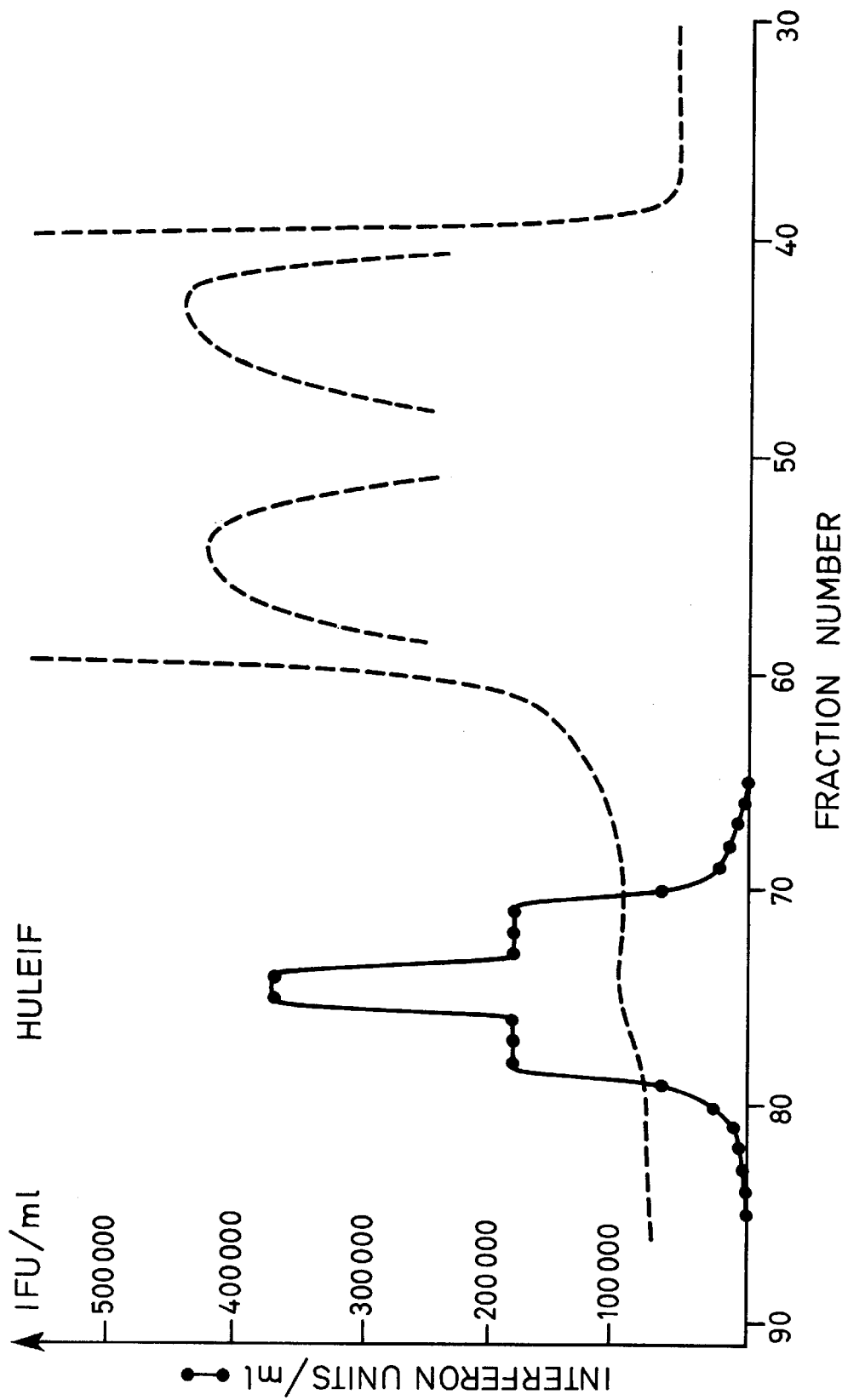
FIG. 5 illustrates a gel filtration curve for crude human leukocyte interferon (HuLeCIF) showing that the interferon activity of human leukocyte interferon (HULEIF) is effectively separate from the major parts of the proteins.
Figure 6:
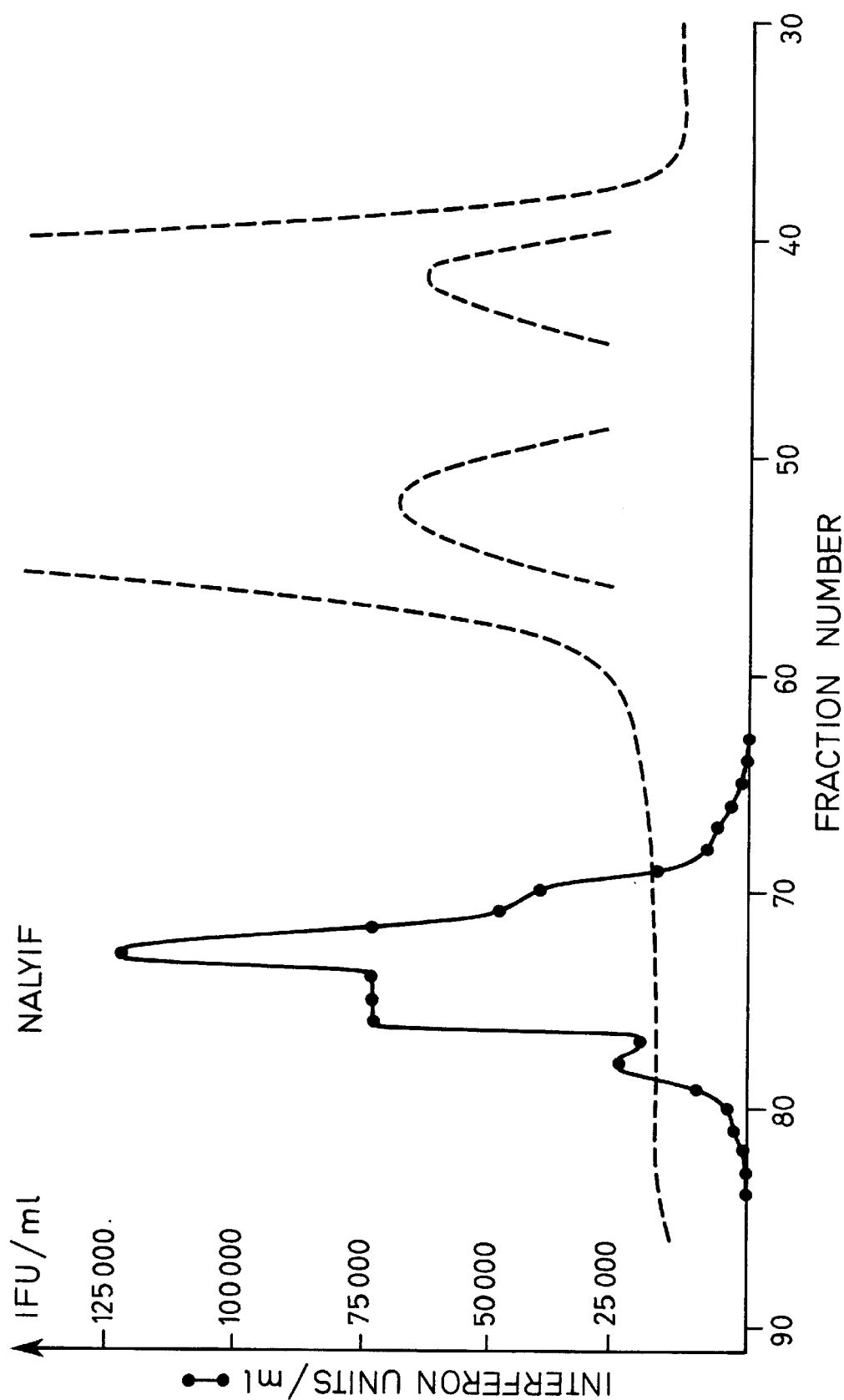
FIG. 6 illustrates a gel filtration curve for crude Namalva interferon (NaCIF) showing that the interferon activity of Namalva interferon (NALYIF) is effectively separate from the major parts of the proteins.

The gel filtration curves for the above-described gel filtration of HuLeCIF and NaCIF are shown in FIGS. 5 and 6, respectively, and "HULEIF" indicates the human leukocyte interferon, whereas "NALYIF" indicates the Namalva (lymphoblastoid) interferon. It is clearly seen that the interferon activity is effectively separated from the major part of the proteins.

Blue Dextran chromatography. The gel-filtered human leukocyte interferon solution, obtained as described above, was exhaustively dialyzed against 200 volumes of 20 mM PB, pH 7.2 at 4° C. The dialysis was performed twice, the total dialysis time being about 24 hours. The dialyzed solution (25 ml, containing $1.8\times10^6$ IFU) was loaded on a column of Blue Dextran-Sepharose 4B. The diameter of the column was 1 cm, and the length of the column was 10 cm. The column was pre-washed with 200–300 ml of 20 mM PB (phosphate buffer) at pH 7.4. The dialyzed interferon preparation was loaded to the equilibrated column, and the column was washed with 75 ml of PB. 4500 IFU was found in the wash. The column was eluted with 0.6 M NaCl, 20 mM PB, pH 7.2 whereby more than 95% of the interferon activity was recovered in 6 ml of eluate, as determined by interferon titration.

Figure 7:
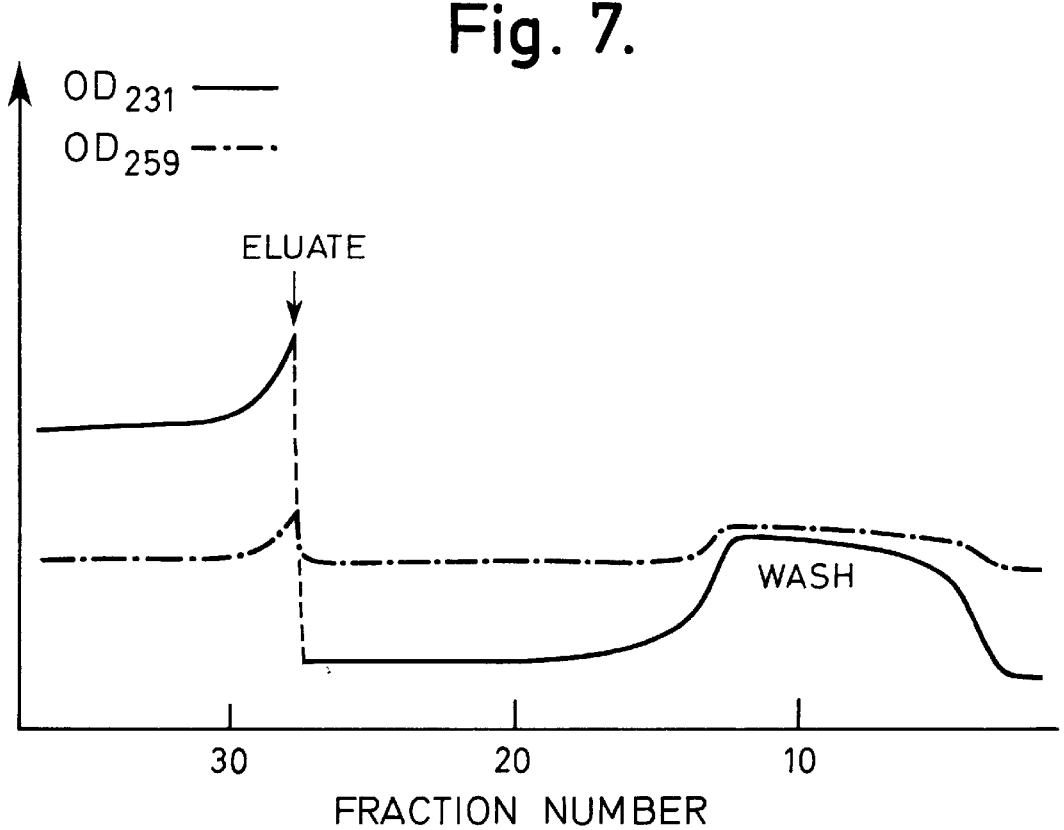
FIG. 7 illustrates the Blue Dextran chromatography of Namalva interferon.

In exactly the same manner, the above-mentioned gel-filtered Namalva interferon solution was exhaustively dialyzed and thereafter subjected to Blue Dextran chromatography. The input in the Blue Dextran chromatography was 1,600,000 IFU. The wash consisted of 70,000 IFU in 50 ml. The eluate was obtained by means of 0.6 M NaCl in PB (pH 7.2). The Blue Dextran chromatography of Namalva interferon is illustrated in FIG. 7. The fibroblast part of the Namalva interferon was not eluted from the column under the above conditions, but is expected to be eluted using, e.g., 25% ethylene glycol in 1 M NaCl, pH 7.2.

The above-mentioned Blue Dextran column was a column of Blue Dextran (Cibacron Blue F3GA immobilized on Dextran 2000 (molecular weight 2 millions)) coupled to cyanogen bromide-activated agarose (Sepharose 4B). Thus, the more complete designation of the column is Blue Dextran-Sepharose 4B. This type of column is described by Bollin et al., loc. cit. After elution, the column was cleaned by elution with 25–30 ml 25% ethylene glycol, 1.5 M NaCl in 20 mM PB. The column was stored in this buffer at 4° C. when not in use. As mentioned above, the loading conditions could also involve the use of hydrophobic reagents, such as alcohols in various amounts (0–50%).

The 0.6 M NaCl eluates from the Blue Dextran chromatography show a specific activity of $70 \times 10^6$ IFU/mg of protein, both for the human leukocyte interferon and for the Namalva interferon. Thus, these are candidates for parenteral administration in human beings for therapeutic purposes and, in this regard, are much more pure preparations than the commonly used PIF preparations. For this use, the eluates are stabilized with physiologically acceptable stabilizers such as described further above, for example 1% of human albumin.

For further purification and for preparation of pure interferon, the eluates from the Blue Dextran column are directly transferred to an antibody affinity chromatography column. In the most advantageous embodiment, the antibody affinity chromatography column is combined with the Blue Dextran column in a "tandem system" as described below:

Tandem Affinity Chromatography. Instead of eluting the Blue Dextran column as described above, the Blue Dextran column is combined with the equilibrated antibody column prior to the elution, by connecting the outlet of the Blue Dextran column with the inlet of the antibody column. In this manner, the eluate from the Blue Dextran column is immediately "caught" by the antibody column. This combination makes use of the fact that the elution conditions (0.6 M NaCl, 20 mM PB, pH 7.2) can be used as loading conditions of the antibody column. After the elution/loading using 20 ml of the eluate/"loading buffer" (this "loading buffer", of course, at the same time contains the interferon eluted from the Blue Dextran column), the two columns are disconnected, and the antibody column is washed further before eluted as described above. The human leukocyte interferon eluate from the antibody column contains pure interferon proteins showing a specific activity of more than $10^9$ IFU/mg of protein (as assessed by the determination method discussed above). For stabilization of the pure interferon proteins, the tubes in which the eluate from the antibody column is collected (fraction size 2 ml) have been pre-wetted with 100 µl of 1% SDS each. After pooling of the interferon-containing eluate, additional SDS is added up to a total concentration of 0.1% by weight.

The pooled interferon-containing eluates stabilized with 0.1% SDS are transferred to a 20 ml stainless steel tube pre-cooled to 0° C. in an ice bath. After 15 minutes, a precipitate is formed. The precipitate is isolated by centrifugation at 20,000 rpm at 4° C. for 20 minutes. The supernatant is discarded (no interferon activity), and the precipitate is redissolved in 4 ml of 8 M urea and transferred to a Millipore concentration cell, size 8 ml, filter 10,000 molecular weight cut, and concentrated to about 100 µl at room temperature. Thereafter, additional 4 ml 4 M urea (p.a.) was added to the concentrate, and the solution was concentrated to about 100 µl at room temperature. 1–3 ml of distilled water was added, and the solution was concentrated again to a volume of 20 µl and mixed with 20 µl SDS sample electrophoresis buffer. 20 µl of the resulting solution was used for characterization as described in the section "SDS PAGE" below.

The above-mentioned antibody affinity chromatography column had been prepared in accordance with "Binding Procedures" using non-monospecific anti-PIF which had been absorbed as follows: a total amount of $10^6$ IFU-NU of anti-interferon immunoglobulins (corresponding to 4 ml sheep anti-interferon serum) was absorbed three times on a 150 ml column of human serum bound to Sepharose 4B followed by 4 absorptions on a CIF-epoxy Sepharose column and 2 absorptions on a CIF CH-activated Sepharose 4B as described in the below section "Absorption of Anti interferon" and in Scand. J. Immunol. 8, 429–436 (1978). Finally, the immunoglobulins had been absorbed on a poly-L-lysine-Sepharose column (once) and on a Soyabean Trypsin Inhibitor-Sepharose column (twice).

Figure 8:
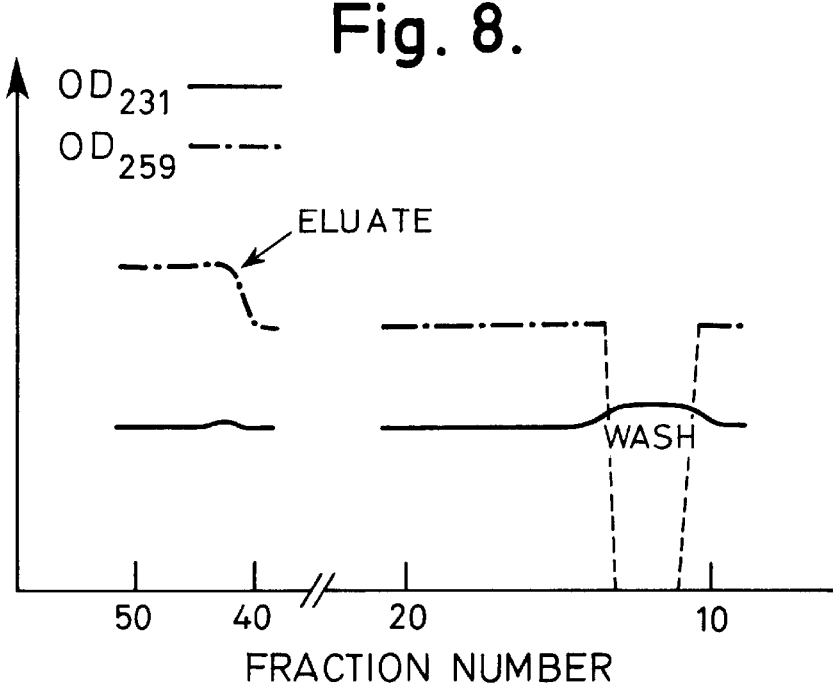
FIG. 8 illustrates the antibody affinity column of the elutate from the Blue Dextran chromatography of Namalva interferon.

The eluate from the Blue Dextran chromatography of Namalva interferon was divided in two portions. One portion was used for SDS PAGE electrophoresis as described below. 250,000 IFU were loaded to the absorbed antibody column as shown in FIG. 8. No interferon was found in the wash. The interferon was eluted as usual by lowering pH to 2.4, and 235,000 IFU (collected in the presence of 0.1% SDS) were recovered. This eluate was concentrated as described above and further examined in SDS PAGE.

SDS PAGE. The SDS PAGE electrophoresis was performed as described under "MATERIALS AND METHODS" above. The stained slab of the electrophoresis of the pure human leukocyte interferon proteins is shown in FIG. 1. FIG. 2 shows, schematically, the stained slab from another experiment, together with the corresponding interferon activity eluted from an unstained parallel gel strip. The striking reproducibility between the two experiments appears from the two Figures, the difference between 20,100 and 20,180 being within the experimental accuracy. As mentioned previously, the biological peaks coincide exactly with the proteins.

From FIG. 1, it appears that the interferon preparation is completely pure by SDS PAGE. There is no other protein band whatsoever visible.

Figure 9:
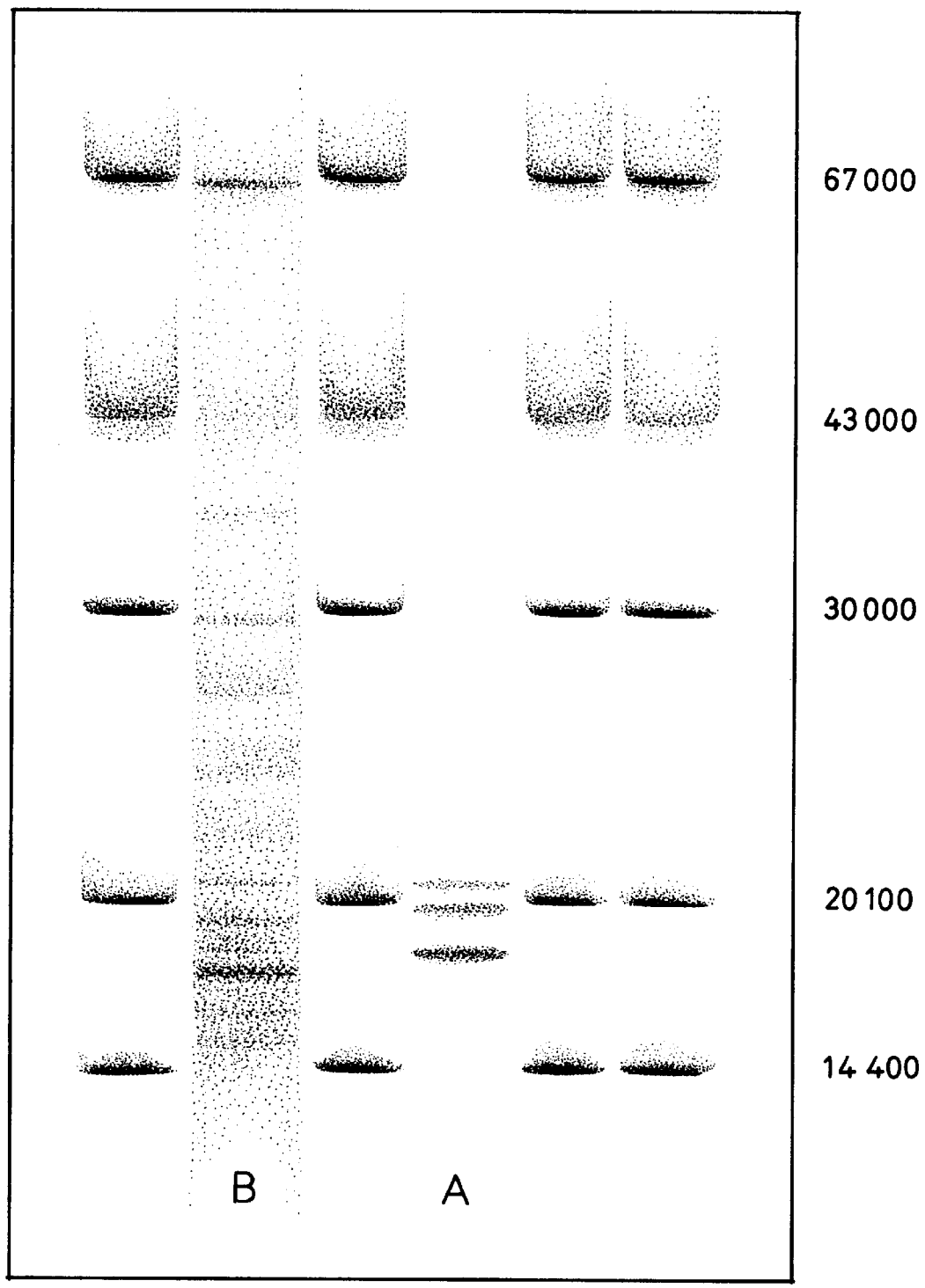
FIG. 9 shows a stained SDS PAGE gel gradient slab of the pure Namalva interferon proteins (A) and of the elutate from the Blue Dextran column (B)

FIG. 9 shows the stained slab from the SDS PAGE (load $0.9 \times 10^6$ IFU), of the pure Namalva interferon proteins (A), and of the eluate from the Blue Dextran column (B). By comparison with FIG. 1, it will be noted that the bands of the pure Namalva interferon are essentially identical with the bands of pure human leukocyte interferon applied in the same amount.

Establishment of Hybridoma Cells with Activity Directed Against Interferon 3 female Balb/c mice, age two months, were immunized with human leukocyte interferon in the following way:

The first injection (40,000 IFU) was performed subcutaneously in the back of each mouse. The immunization was continued every week with subcutaneous injection of 70,000 IFU. The last injection was given intravenously the 9th week (mouse 1) and 10th week (mouses 2 and 3), respectively.

The development of anti-interferon was determined on serum samples from the mice, using the interferon neutralization test. As a laboratory check of the interferon neutralization test system, an internal anti-interferon IgG preparation (raised by injecting rabbits with partially purified human leukocyte interferon preparations) was, as usually, included. The serum samples from the mice showed no anti-interferon activity the first six weeks. Thereafter, distinct anti-interferon activity was found:

TABLE I

| | IFU-NU per ml | | | |
|---|---|---|---|---|
| | 7th week | 8th week | 9th week | 10th week |
| mouse 1 | 160 | 160 | 120 | — |
| mouse 2 | 200 | 1280 | 2500 | 1200–2500 |
| mouse 3 | 80 | 40 | 40 | 5–10 |

The mice were killed by breaking their necks two to four days after the last injection, and their spleens were removed under sterile conditions. After homogenization of each spleen in PBS, the homogenized cell suspension was transferred to centrifuge tubes and centrifugated for 5 minutes at 170 g at 4° C. The cells were resuspended in PBS, and after a second centrifugation, they were resuspended in serum-free DMEM (about 0.5 ml per spleen). The total amount of cells was $10^8$ (mouse 1), $0.8 \times 10^8$ (mouse 2), and $0.8 \times 10^8$ (mouse 3). The viability was around 85–90%.

By treatment with polyethylene glycol in the manner described below, the spleen cell suspension from each mouse was fused with $10^7$ X63Ag8 (HPRT-) myeloma cells in the following manner: $10^8$ mouse spleen cells and $10^7$ 8-azaguanin-resistent myeloma cells (X63Ag8; NSI/1Ag 4-1; SP 2/0-Ag 14) were mixed in a 50 ml conical plastic centrifuge tube (Falcon 2070). The tube was filled up with serum-free DMEM and centrifugated for 10 minutes at 170–200 g and 4° C. The supernatant was carefully removed, and at 37° C., a total of 0.7 ml of 50% polyethylene glycol solution having a temperature of 37° C. was added dropwise over a period of 1 minute with gentle rotation. After incubation for 90 seconds at 37° C., 15 ml of warm serum-free DMEM were added very slowly (in the course of 1–2 minutes). Thereafter, the mixture was centrifugated for 10 minutes at 200 g, and the cell pellet was resuspended in 50 ml complete DMEM-FCS for seeding in Costar trays.

From each of the fusions, 48 cultures, each of 1 ml, were seeded in Costar trays (2 trays, each with 24 holes per spleen=48 cultures per mouse). After 10–15 days, growth was noted in 21 cultures (mouse 1), 0 cultures (mouse 2) and (after further seeding out) 150 cultures (mouse 3).

The cells were transferred to 5 ml cultures in 25 ml NUNC bottles which, like the Costar trays, contained a "feeder layer" of macrophages. On shift of medium, the supernatants were obtained, and from these dense cultures, cells were frozen in liquid nitrogen.

The supernatants of the individual cultures from mouse 1 were subjected to detection of positive clones using the interferon neutralization test. In this manner, one positive clone was found, although with a very low titer (about 2–3 IFU-NU per ml).

Production of Anti-Interferon by Means of Pure Interferon Proteins (Pure by SDS PAGE)

The eluate from the above-described tandem affinity chromatography, as characterized by SDS PAGE, was used for immunization of rabbits as follows:

About 1,000,000 IFU units were concentrates to about 1 ml and dialyzed against PBS at 10° C. overnight. Two rabbits were injected subcutaneously with each 1,000,000 IFU prepared in this manner. The injection was repeated each second week. The development of antibodies appears from Table II:

TABLE II

| | NEUTRALIZATION UNITS (IFU-NU) | | | | | | | | |
|---|---|---|---|---|---|---|---|---|---|
| | | | | | Freund's adjuvant ↓ | | | | |
| Rabbit I | xx) | 1 | 3 | 5 | 7 | 9 | 11 | 13 | 15 |
| | xxx) | 0 | 0 | 2 | 100 | 2000 | ND$^{x)}$ | 20,000 | 20,000 |

TABLE II-continued

NEUTRALIZATION UNITS (IFU-NU)

Freund's adjuvant ↓

| | | | | | | | |
|---|---|---|---|---|---|---|---|
| Rabbit I | xx) | 17 | 19 | 21 | 23 | 25 | 27 |
| | xxx) | 20,000 | 800,000 | 600,000 | 500,000 | 600,000 | 600,000 |

Freund's adjuvant ↓

| | | | | | | | |
|---|---|---|---|---|---|---|---|
| Rabbit II | xx) | 1 3 5 | 7 | 9 | 11 | 13 | 15 |
| | xxx) | 0 0 0 | 20 | 500 | ND$^{x)}$ | 20,000 | 10,000 |

Freund's adjuvant ↓

| | | | | | | | |
|---|---|---|---|---|---|---|---|
| Rabbit II | xx) | 17 | 19 | 21 | 23 | 25 | 27 |
| | xxx) | 8000 | 100,000 | 150,000 | 200,000 | 180,000 | 185,000 | x) not determined
xx) week
xxx) antiinterferon titers (IFU-NU/ml)

Production of Anti-Interferon by Means of Pure Stained Interferon Proteins Cut Out From an SDS PAGE The immunization was performed according to the protocol explained on page 11 of the present specification, using the minced interferon-containing (and partially washed and destained) gel suspension directly as the immunogenic preparation. One rabbit (III) was immunized with the 18,400±200 Daltons species, and another rabbit (IV) was immunized with the 20,100±200 Daltons species (died after week 15). Good results were obtained, vide Table III:

TABLE III

NEUTRALIZATION UNITS

Freund's adjuvant ↓

| | | | | | | | | |
|---|---|---|---|---|---|---|---|---|
| Rabbit III (18,4000 | week | 1 | 3 | 5 | 7 | 9 | 11 | 15 |
| Daltons species) | IFU-NU/ml | 0 | 0 | 0 | 1–2 | 2 | 2 | 200 |
| Rabbit IV (20,100 | week | 1 | 3 | 5 | 7 | 9 | 11 | 15 |
| Daltons species) | IFU-NU/ml | 0 | 0 | 0 | 0 | 1 | 2 | 200 |

Antigenicity of the 18,400 Daltons Species Versus the 20,100 Daltons Species and Vice Versa In order to show that the antigenic determinants of the above-mentioned two species are identical, the following cross-neutralization experiments were performed:

Interferon protein was eluted from the 18,400±200 Daltons species SDS PAGE band and the 20,100±200 Daltons species SDS PAGE band in the manner described above, and solutions containing 5–10 IFU of the two species were prepared. Solutions of anti-interferon from the two species, prepared in rabbits as described above, were diluted to contain 20 IFU-NU in total/ml. Aliquots (1 ml) of pure interferon species containing 10 IFU of the 18,400 Daltons interferon species and 10 IFU of the 20,100 Daltons interferon species, respectively, were mixed with 1 ml solution of the 18,400 Daltons species anti-interferon and 1 ml solution of the 20,100 Daltons species anti-interferon, respectively, in all possible permutations, that is, the anti-interferon of each species was mixed with the interferon of both species separately. After 1 hour at 37° C., any remaining interferon activity was determined by performing the usual interferon titration (vide "Materials and Methods" above). No interferon activity was found. Thus, when mixing the 18,400±200 Daltons species and the 20,100±200 Daltons species, respectively, with each of the anti-18,400±200 Daltons species and the anti-20,100±200 Daltons species, separately, and vice versa, no interferon was detected, in other words, a complete neutralization had occurred. Therefore, it can be concluded that the two interferon species exhibit the same antigenic determinants. This implies that the anti-18,400±200 Daltons species will be useable as a monospecific antibody for purification of both interferon species, and the same applies for the anti-20,100±200 Daltons species, and for a mixture of the two species. Further experiments performed in the same manner showed that each of the six biological peaks was completely neutralized by each of the antisera raised against the two major species.

It is highly likely that the two major species isolated from the Namalva SDS PAGE will give the same result, in other words, that they also cross-react and show identity to HuLeIf in terms of antigenicity. (HuLeIF 18,400±200 being identical to Namalva 18,400±200, both with respect to antigenicity and molecular weight, and HuLeIF 20,100±200 being similarly identical with Namalva 20,100±200).

Biological Effects of the Pure Interferon Proteins

Antiviral Activity

The antiviral activity of each of the six stained protein bands shown in FIG. 3 was determined. The gel was loaded in two slots, both of which were stained. The stained bands in one of the slots is shown at A in FIG. 3. The other slot slot was then briefly destained (in 50% methanol, 45% $H_2O_2$, 5% acetic acid), the exact location of the interferon proteins in the wet gel was recorded, and the gel was rinsed in water and was thereafter sliced as shown at B in FIG. 3. The number of gel slices is indicated at C in FIG. 3. In this manner, each interferon protein band was exactly cut out of the gel, without being mixed with the adjacent one. Each slice was eluted in the same manner as described in the section "Materials and Methods", and the biological profile shown in FIG. 3 was constructed using the usual interferon titration described in "Material and Methods". The neutralizing activity of each of the six species cut out and eluted from the SDS PAGE was checked against anti-leukocyte interferon, and it was found that all of the species were completely neutralized by the same anti-serum. The recovery of interferon in FIG. 3 was rather low (20%) compared with normal "SDS PAGE elution" without pre-staining (except for the 18,400±200 Daltons species), which indicates that the biological activity of most of the interferon species was selectively destroyed compared with the antigenicity. In the neutralization tests against anti-leukocyte interferon, the interferon proteins "eluted from FIG. 3" were able to neutralize the anti-leukocyte interferon 3–5 times more effectively than native (crude) human leukocyte interferon, calculated on interferon activity basis, which indicates a selective destruction of determinants responsible for the biological activity.

Non-Antiviral Effects

The non-antiviral effects of the pure human leukocyte interferon species were checked in 3 systems:
1) Anti-cellular activity.

The anticellular activity of the pure interferon proteins was investigated by incubating Daudi cells with 1:1000 dilutions (in medium) of pure interferon proteins obtained from the eluted SDS PAGE fractions as shown in FIG. 2, by ascertaining the relative depression of Tritium labelled Thymidine (I. Heron and K. Berg, The actions of interferon are potentiated at elevated temperature, Nature, 274, 508–510 (1978)) compared to controls without interferon (FIG. 2, upper part, where "% G-I" designates % growth inhibition). As can be clearly seen, the "anticellular curve" follows the antiviral curve very strictly. This proves that all the five species of pure native human leukocyte interferon contain both the antiviral activity and the anticellular activity. The peak size of the different "anticellular peaks" does not vary linearly with the corresponding size of the "interferon peaks", which probably reflects the sensitivity of the Daudi cell system (J. Hilfenhaus, H. Damm, H. E. Karges and K. E. Manthey, Growth inhibition of human lymphoblastoid Daudi cells in vitro by interferon preparations, Arch. Virol. 51, 87–97 (1976). The small interferon peak at 19,500 Daltons gave no rise to a corresponding peak in the anticellular curve. At a 10-fold lower dilution (1:100), however, a small but distinct peak of anticellular activity was also observed (not shown).
2) The expression of major histocompatibility antigen (MHC) on lymphocytes and monocytes.

The selective increase in $\beta_2$-associated MHC (major histocompatibility antigen) expression was observed using partially purified human leukocyte interferon, such as described by I. Heron, M. Hokland & K. Berg (1978), "Enhanced expression of $\beta_2$ microglobulin and HLA on human lymphoid cells by interferon", Proc. Natl. Acad. Sci. 75: 6215–6222 (referred to below as PNAS 75). Each of the two major human leukocyte interferon species (18,400 and 20,100 Daltons, vide FIG. 1), was assayed in doses around 100 IFU per ml culture medium. The above-mentioned effect was found using these pure molecular species, whereas eluates from gel slices outside the regions where antiviral activity was recorded had no effect. It has, thus, been proved that the effect of selective enhancement of MHC antigen expression on lymphoid cells is an inherent feature of the interferon molecules.
3) The potentiation of the Natural Killer cell system (NK system).

Figure 10:
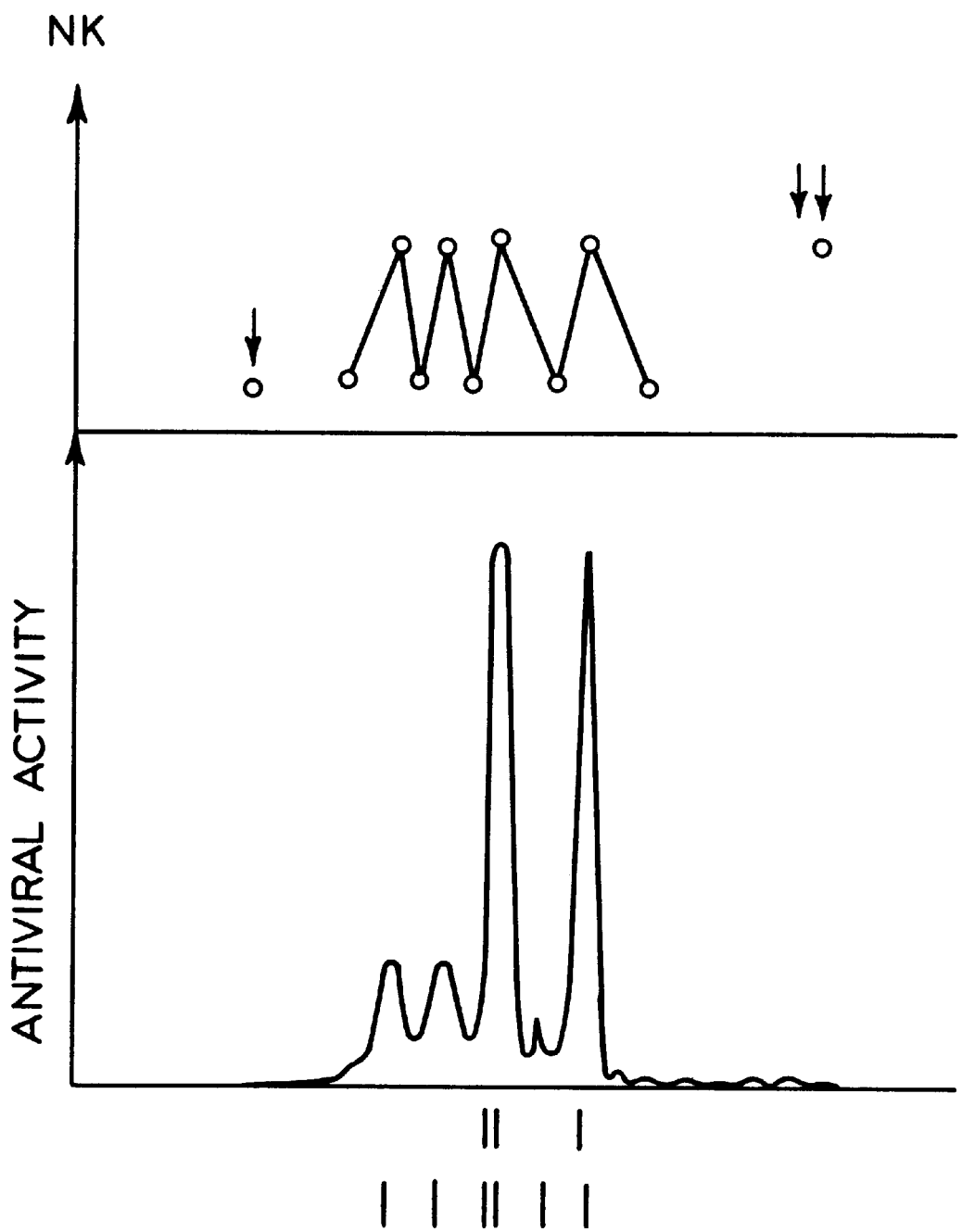
FIG. 10 shows the antiviral activity profile of 5–6 bands of pure human leukocyte interferon as assessed on an SDS PAGE in the same manner as described in connection with FIG. 2.

FIG. 10 shows the antiviral profile (as assessed on an SDS PAGE in the same manner as described in connection with FIG. 2). Each of the species from the gel was assessed for NK enhancing activity, using the method described in PNAS 75. Fractions that have anti-viral activity as shown in the lower curve gave increased NK, such as illustrated in the upper curve, whereas "base line" fractions did not. One arrow indicates only saline added as a negative control, and two arrows indicate partially purified human leukocyte interferon (PIF) used as a positive control. Around 100 IFU antiviral units of each interferon preparation was added per ml.

ABSORPTION OF ANTI-INTERFERON

In accordance with one aspect of the present invention, the absorption of anti-interferon by means of matrix-immobilized crude human non-fibroblast interferon constitutes a method of broad applicability for establishing highly specific anti-interferon which, when immobilized on a matrix, is an extremely valuable tool for purifying interferon to a high degree. In the experiments reported below, the features of this aspect of the invention are illustrated in greater detail:

A column of CIF-epoxy-Sepharose was constructed using 20 ml of CIF with a titre of 300,000 IFU/ml according to the procedure described by the manufacturer (Pharmacia), using 0.1 M $NaHCO_3$/0.3 M NaCl as coupling buffer. 55% of the proteins were coupled. 0.5 ml of anti-interferon (150,000 interferon-neutralizing units (IFU-NU/ml) was applied to the column, and the qualitative results were similar to those obtained with the CIF-CH-activated Sepharose column below: almost all the anti-interferon appeared in the wash; 5000 IFU-NU were found in the first eluate (pH 2.4).

A column of crude concentrated human leukocyte interferon (CIF) on activated CH-Sepharose 4B was constructed using 5 ml CIF in the manner described by the manufacturer (Pharmacia), using 0.1 M $NaHCO_3$/0.1 M NaCl as coupling buffer. 53% of the proteins were coupled. The column was loaded with 1 ml anti-interferon with a titre of 150,000 IFU-NU per ml, using as loading buffer 0.1 M NaOAc/0.3 M NaCl, pH 7.0. The major part of the anti-interferon activity passed through the column (more than 95%). The column was eluted with 0.1 M HOAc/0.3 M NaCl, pH 2.4.

About 5 mg of immunoglobulins were removed in this eluate together with about 10,000 IFU-NU. Thereafter, it was tried to elute with 4 M urea in PBS including 0.1% ethanolamine (pH 6.0), and this eluted more proteins together with about 3000–4000 IFU-NU, but the capacity of the column was partially destroyed by urea, and elution with urea was therefore abandoned, and a new column was made.

The CIF used in the construction of the two above-mentioned columns was prepared by concentrating crude interferon made as described under "MATERIALS AND METHODS" above 10–20 times by means of 0.5 M KSCN at pH 3.5 followed by a dialysis vs. coupling buffer.

Instead of CIF it would also be within the scope of the invention to use "washes" from "interferon antibody affinity chromatographies", in particular interferon antibody affinity chromatographies performed using the monospecific antibodies of the invention. Also, all the impurities could be pooled together from several interferon antibody affinity chromatographies, and these impurities could be used instead of or combined with CIF.

Absorption of Anti-interferon. 2 ml of anti-interferon, containing 450,000 IFU-NU/ml and 100 mg immunoglobulins, were first loaded on the CIF-epoxy-Sepharose column whereby 30% of the immunoglobulins were removed together with 25,000 IFU-NU of the anti-interferon activity (i.e., 2.7% of the input). The wash was concentrated, dialysed vs. loading buffer (same as described above) and reapplied to the equilibrated column; this time only 3.5 mg of immunoglobulins were removed, while the same amount of anti-interferon was retained. The antibodies were passed through the column eight times. About 40% of the immunoglobulins had been removed at this stage together with 15% of the anti-interferon activity (which could be recovered in the eluates). This absorbed anti-interferon preparation was then applied to the CIF-CH-activated Sepharose column, and about 1600 µg were removed together with 35,000 IFU-NU. The procedure was repeated three times. The last wash had a total content of 320,000 IFU-NU and 22 mg proteins. This purified anti-interferon was absorbed on a Poly-L-Lysine and Soya Bean Trypsin Inhibitor column as described above and was then coupled covalently to Sepharose 4B in accordance with "Binding Procedures", binding 85% of the immunoglobulins. In addition, two other sheep-anti-interferon batches (titres 120,000 IFU-NU/ml and 100,000 IFU-NU/ml) were also absorbed with similar results. These sera were absorbed only eight times in total, and above 35% of the immunoglobulins were removed together with about 10–15% of the anti-interferon activity. Rabbit anti-interferon serum was also absorbed. Since the titres thereof were rather low (10,000 and 25,000 IFU-NU/ml), the batches were first concentrated 10-fold and 5-fold, respectively. After five absorptions, about 45% of the immunoglobulins were removed together with 25% of the anti-interferon activity. All anti-interferon preparations were made as described in the above section "Non-monospecific anti-interferon".

Purification of Various Interferons by Antibody Affinity Chromatography Using Absorbed Anti-Interferon A "control" column (not according to the invention) was constructed with unabsorbed anti-interferon and loaded with 2.5 ml of CIF containing in total $1.2 \times 10^6$ IFU. The wash contained $5.5 \times 10^5$ IFU/20 ml, and the eluate contained $3 \times 10^6$ IFU/10 ml. There was an obvious discrepancy between the protein peak and the interferon peak in the eluate. A great amount of impurity was eluted under very mild elution conditions (pH 4.5). The quantitative data of the experiment appear from the below Table IV. The specific activity of the protein in the eluate was only about $0.9 \times 10^5$ IFU/mg protein.

In accordance with the present invention, the Sepharose 4B column coupled with the purified anti-interferon as described in the above section "Absorption of Anti-interferon" was loaded with 5 ml CIF (crude concentrated human leukocyte interferon). The input contained $3 \times 10^6$ IFU in total, the wash contained $3 \times 10^5$ IFU/20 ml, and the eluate contained $4 \times 10^6$ IFU/6 ml. Like in the control experiment described above, the fraction size was 2 ml, and the loading and elution buffers were the same as mentioned above, i.e., loading buffer 0.1 M NaOAc/0.3 M NaCl, pH 7.0, elution buffer 0.1 M HOAc/0.3 M NaCl, pH 2.4. The specific activity in the eluted material was found to be $43 \times 10^6$ IFU/mg.

Crude Namalva interferon was also purified up to the same level as normal crude leukocyte interferon, using the same column (Table IV, Experiments 5 and 6).

Human fibroblast interferon was purified (Table IV, Experiment 7) in one step up to $2 \times 10^8$ IFU/mg protein (peak fraction), with a recovery of 90%. On a subsequent SDS-PAGE, it was revealed that the preparation contained 4 bands with a faint band barely visible at the interferon region.

Partially purified human interferon (PIF) with an initial specific activity close to $1 \times 10^6$ IFU/mg protein was loaded to the column. The results are shown in Table V: Only 3000 IFU were found in the wash, which corresponds to less than 0.25%; the recovery obtained was 80% based on the eluate pool. The highest specific activity was about $10^8$ IFU/mg protein (fraction 25, Table V).

TABLE IV

Purification of human interferons by antibody affinity chromatography

| Experiment No. | Type of interferon | Input IFU** total ($\times 10^{-6}$) | Vol. (ml) | Spec. act. of input (IFU/mg) | Wash total (IFU) | Eluate total (IFU $\times 10^{-6}$) | Eluate† total prot. (µg) | Spec. act. of eluate (IFU/mg $\times 10^{-6}$) | Spec. act. peak fraction (IFU/mg $\times 10^{-6}$) | Recovery (%)** | Purification factor |
|---|---|---|---|---|---|---|---|---|---|---|---|
| 1* | Crude leucocyte | 1.2 | 2.5 | $10^4$ | $5.5 \times 10^5$ | 1.6† | 1812 | 0.88 | †† | 133 | 88** |
| 2§ | Crude leucocyte | 3 | 3.0 | $10^4$ | $8 \times 10^5$ | 4.2: | 98 | 43 | 60 | 140 | 6000¶ |
| 3§ | Crude leucocyte | 1.5 | 2.5 | $10^4$ | $6 \times 10^5$ | 1.8: | 55 | 33 | 40 | 120 | 4000¶ |
| 4§ | Crude leucocyte | 2 | 5.0 | $10^4$ | $6 \times 10^5$ | 2.4: | 78 | 31 | †† | 120 | 3100** |
| 5§ | Crude Namalva | 1.6 | 150 | $6 \times 10^3$ | $1.7 \times 10^4$ | 2.6 | 115 | 23 | †† | 163 | 3800** |

TABLE IV-continued

Purification of human interferons by antibody affinity chromatography

| Experiment No. | Type of interferon | Input IFU[:] total (× $10^{-6}$) | Vol. (ml) | Spec. act. of input (IFU/mg) | Wash total (IFU) | Eluate total (IFU × $10^{-6}$) | Eluate† total prot. (μg) | Spec. act. of eluate (IFU/mg × $10^{-6}$) | Spec. act. peak fraction (IFU/mg × $10^{-6}$) | Recovery (%)** | Purification factor |
|---|---|---|---|---|---|---|---|---|---|---|---|
| 6§ | Crude Namalva | 1.05 | 150 | $4 \times 10^3$ | $8 \times 10^4$ | 0.95 | 110 | 8.6 | 16 | 90 | 4000¶ |
| 7§ | Human fibroblast | 4 | 50 | $8 \times 10^5$ | $8 \times 10^5$ | 3.6 | 35† | 103 | 200 | 90 | 250¶ |

*Column with unabsorbed interferon.
†Based in individual determinations of the fractions.
:After addition of SDS to 0.1% SDS.
§Column with with absorbed antiinterferon as described in the above section "Absorption of Antiinterferon".
¶Based on specific activity of peak fraction.
**Based on eluate.
††Not detected.
[:]IFU interferon units, measured as international reference units 69/19B.

TABLE V

Purification of partially purified human interferon (PIF) ⚹

| | IFU | Vol. (ml) | Total proteins (/ug) | Spec. act. (IFU/mg protein) | pH |
|---|---|---|---|---|---|
| Input | $1.5 \times 10^6$ | 0.9 | 1300 | $1.2 \times 10^6$ | 7 |
| Wash | 3000 | 20 | N.D.: | N.D. | 7 |
| No. 23 | $8 \times 10^5$ | 2 | 10 | $2.5 \times 10^7$ | 4.7 |
| No. 24 | $8 \times 10^5$ | 2 | 16 | $5 \times 10^7$ | 3.3 |
| No. 25 | $1.2 \times 10^5$ | 2 | 6 | $1.3 \times 10^8$ | 2.7 |
| No. 26 | $1.2 \times 10^6$ | 2 | <2 | $>6 \times 10^7$ | 2.5 |
| Eluate pool | $1.9 \times 10^6$ | 10 | 35 | $3.4 \times 10^7$ | N.D. |
| Eluate pool† | | 10 | 32 | $5.9 \times 10^7$ | N.D. |

⚹Experiment No 318 (PIF = partially purified human leucocyte interferon).
†Based on individual fraction
: N.D. = not detected.
§IFU = interferon units in international reference units 69/19B.

I claim:

1. A species of human leukocyte interferon having a molecular weight of 20,180±200 daltons under non-reducing SDS PAGE, and a specific activity of from about $2 \times 10^8$ to about $2 \times 10^9$ IFU per mg of protein.

2. The species of human leukocyte interferon of claim 1 having a specific activity of about $2 \times 10^8$ IFU per mg of protein.

3. The species of human leukocyte interferon of claim 1 having a specific activity of about $10^9$ IFU per mg of protein.

4. The species of human leukocyte interferon of claim 1 having a specific activity of $2 \times 10^9$ IFU per mg of protein.

5. The species of human leukocyte interferon of claim 1 having a specific activity of from $2 \times 10^8$ to $2 \times 10^9$ IFU per mg of protein.

6. A species of human leukocyte interferon having a molecular weight of 20,180±200 daltons under non-reducing SDS PAGE, and a specific activity of at least $2 \times 10^8$ IFU per mg of protein.

7. The species of human leukocyte interferon of claim 6 having a specific activity of at least $10^9$ IFU per mg of protein.

8. A species of human leukocyte interferon having a molecular weight of 19,500±200 daltons under non-reducing SDS PAGE, and a specific activity of from about $2 \times 10^8$ to about $2 \times 10^9$ IFU per mg of protein.

9. The species of human leukocyte interferon of claim 8 having a specific activity of about $2 \times 10^8$ IFU per mg of protein.

10. The species of human leukocyte interferon of claim 8 having a specific activity of about $10^9$ IFU per mg of protein.

11. The species of human leukocyte interferon of claim 8 having a specific activity of $2 \times 10^9$ IFU per mg of protein.

12. The species of human leukocyte interferon of claim 8 having a specific activity of from $2 \times 10^8$ to $2 \times 10^9$ IFU per mg of protein.

13. A species of human leukocyte interferon having a molecular weight of 19,500±200 daltons under non-reducing SDS PAGE, and a specific activity of at least $2 \times 10^8$ IFU per mg of protein.

14. The species of human leukocyte interferon of claim 13 having a specific activity of at least $10^9$ IFU per mg of protein.

15. A species of human leukocyte interferon having a molecular weight of 20,420±200 daltons under non-reducing SDS PAGE, and a specific activity of from about $2 \times 10^8$ to about $2 \times 10^9$ IFU per mg of protein.

16. The species of human leukocyte interferon of claim 15 having a specific activity of about $2 \times 10^8$ IFU per mg of protein.

17. The species of human leukocyte interferon of claim 15 having a specific activity of about $10^9$ IFU per mg of protein.

18. The species of human leukocyte interferon of claim 15 having a specific activity of $2 \times 10^9$ IFU per mg of protein.

19. The species of human leukocyte interferon of claim 15 having a specific activity of from $2 \times 10^8$ to $2 \times 10^9$ IFU per mg of protein.

20. A species of human leukocyte interferon having a molecular weight of 20,420±200 daltons under non-reducing SDS PAGE, and a specific activity of at least $2 \times 10^8$ IFU per mg of protein.

21. The species of human leukocyte interferon of claim 20 having a specific activity of at least $10^9$ IFU per mg of protein.

22. The species of human leukocyte interferon of any one of claims 1, 6, 8, 13, 15 and 20, obtained from lymphoblastoid cells.

23. The species of human leukocyte interferon of any one of claims 1, 6, 8, 13, 15 and 20 obtained from Namalva cells.

24. A species of human leukocyte interferon obtained from lymphoblastoid cells, having a molecular weight of 21,130±200 daltons under non-reducing SDS PAGE, and having a specific activity of from about $2 \times 10^8$ to about $2 \times 10^9$ IFU per mg of protein.

25. The species of human leukocyte interferon of claim 24 having a specific activity of about $2 \times 10^8$ IFU per mg of protein.

26. The species of human leukocyte interferon of claim 24 having a specific activity of about $10^9$ IFU per mg of protein.

27. The species of human leukocyte interferon of claim 24 having a specific activity of $2 \times 10^9$ IFU per mg of protein.

28. The species of human leukocyte interferon of claim 24 having a specific activity of from $2 \times 10^8$ to $2 \times 10^9$ IFU per mg of protein.

29. The species of human leukocyte interferon of claim 24, wherein said lymphoblastoid cells are Namalva cells.

30. A species of human leukocyte interferon obtained from lymphoblastoid cells, having a molecular weight of 21,130±200 daltons under non-reducing SDS PAGE, and having a specific activity of at least $2 \times 10^8$ per mg of protein.

31. The species of human leukocyte interferon of claim 30 having a specific activity of at least $10^9$ IFU per mg of protein.

32. The species of human leukocyte interferon of claim 30, wherein said lymphoblastoid cells are Namalva cells.

33. A species of human leukocyte interferon obtained from lymphoblastoid cells, having a molecular weight of 23,440±200 daltons under non-reducing SDS PAGE, and having a specific activity of from about $2 \times 10^8$ to about $2 \times 10^9$ IFU per mg of protein.

34. The species of human leukocyte interferon of claim 33 having a specific activity of about $2 \times 10^8$ IFU per mg of protein.

35. The species of human leukocyte interferon of claim 33 having a specific activity of about $10^9$ IFU per mg of protein.

36. The species of human leukocyte interferon of claim 33 having a specific activity of $2 \times 10^9$ IFU per mg of protein.

37. The species of human leukocyte interferon of claim 33 having a specific activity of from $2 \times 10^8$ to $2 \times 10^9$ IFU per mg of protein.

38. The species of human leukocyte interferon of claim 33, wherein said lymphoblastoid cells are Namalva cells.

39. A species of human leukocyte interferon obtained from lymphoblastoid cells, having a molecular weight of 23,440±200 daltons under non-reducing SDS PAGE, and having a specific activity of at least $2 \times 10^8$ IFU per mg of protein.

40. The species of human leukocyte interferon of claim 39 having a specific activity of at least $10^9$ IFU per mg of protein.

41. The species of human leukocyte interferon of claim 39, wherein said lymphoblastoid cells are Namalva cells.

42. A species of human leukocyte interferon obtained from lymphoblastoid cells, having a molecular weight of 18,400±200 daltons under non-reducing SDS PAGE, and having a specific activity of from about $2 \times 10^8$ to about $2 \times 10^9$ IFU per mg of protein.

43. The species of human leukocyte interferon of claim 42 having a specific activity of about $2 \times 10^8$ IFU per mg of protein.

44. The species of human leukocyte interferon of claim 42 having a specific activity of about $10^9$ IFU per mg of protein.

45. The species of human leukocyte interferon of claim 42 having a specific activity of $2 \times 10^9$ IFU per mg of protein.

46. The species of human leukocyte interferon of claim 42 having a specific activity of from $2 \times 10^8$ to $2 \times 10^9$ IFU per mg of protein.

47. A species of human leukocyte interferon obtained from lymphoblastoid cells, having a molecular weight of 18,400±200 daltons under non-reducing SDS PAGE, and having a specific activity of at least $2 \times 10^8$ IFU per mg of protein.

48. The species of human leukocyte interferon of claim 47 having a specific activity of at least $10^9$ IFU per mg of protein.

49. A formulation consisting essentially of the species of human leukocyte interferon of any one of claims 1, 8, 15, 24, 33 and 42 and a carrier.

50. The formulation of claim 49 further comprising a stabilizer.

51. The formulation of claim 50 wherein the stabilizer comprises human albumin.

52. The formulation of claim 50 wherein the stabilizer comprises a human serum protein.

53. The formulation of claim 50 wherein said stabilizer is sodium dodecyl sulfate.

54. The formulation of claim 49 wherein said species of human leukocyte interferon is present in an amount effective to achieve a prophylactic, therapeutic or immunization effect upon administration to a human.

55. The formulation of claim 49 wherein the carrier is aqueous.

56. The formulation of claim 49 adapted for parenteral, intranasal or topical administration.

57. A method of making a formulation comprising combining the interferon of any one of claims 1, 8, 15, 24, 33 and 42 with a carrier.

58. The method of claim 57 further comprising adding a stabilizer.

59. The method of claim 58 wherein the carrier comprises human albumin.

60. The method of claim 58 wherein the stabilizer comprises a human serum protein.

61. The method of claim 58 wherein the stabilizer comprises sodium dodecyl sulfate.

62. The method of claim 57 wherein the carrier is aqueous.

63. Human leukocyte interferon protein, prepared by:
   (a) applying a solution of human leukocyte interferon obtained from lymphoblastoid cells to a matrix having immobilized thereon monospecific antibodies that bind human leukocyte interferon protein, wherein said antibodies are raised against a species of human leukocyte interferon selected from the group consisting of the human leukocyte interferon species having molecular weights of 18,400±200 daltons, 19,500±200 daltons, 20,180±200 daltons, 20,420±200 daltons, 21,130±200 daltons and 23,440±200 daltons, said molecular weights measured under non-reducing SDS-PAGE; and
   (b) eluting said human leukocyte interferon protein from the matrix, wherein said human leukocyte interferon protein eluted from the matrix comprises at least one species of human leukocyte interferon protein selected from the group consisting of the human leukocyte interferon species having molecular weights of 18,400±200 daltons, 19,500±200 daltons, 20,180±200 daltons, 20,420±200 daltons, 21,130±200 daltons and 23,440±200 daltons, said molecular weights measured under non-reducing SDS-PAGE, and having a specific activity of more than $2 \times 10^8$ IFU per mg of protein.

64. The human leukocyte interferon of claim 63 having a specific activity of about $10^9$ IFU per mg protein.

65. The human leukocyte interferon of claim 63 having a specific activity of at least $10^9$ IFU per mg protein.

66. The human leukocyte interferon of claim 63 having a specific activity of $2 \times 10^9$ IFU per mg of protein.

67. Human leukocyte interferon protein, prepared by:
   (a) applying a solution of human leukocyte interferon obtained from Namalva cells to a matrix having immobilized thereon monospecific antibodies that bind human leukocyte interferon protein, wherein said antibodies are raised against a species of human leukocyte interferon selected from the group consisting of the human leukocyte interferon species having molecular weights of 18,400±200 daltons, 19,500±200 daltons, 20,180±200 daltons, 20,420±200 daltons, 21,130±200 daltons and 23,440±200 daltons, said molecular weights measured under non-reducing SDS-PAGE; and (b) eluting said human leukocyte interferon protein from the matrix, wherein said human leukocyte interferon protein eluted from the matrix comprises at least one species of human leukocyte interferon protein selected from the group consisting of the human leukocyte interferon species having molecular weights of 18,400±200 daltons, 19,500±200 daltons, 20,180±200 daltons, 20,420±200 daltons, 21,130±200 daltons and 23,440±200 daltons, said molecular weights measured under non-reducing SDS-PAGE, and having a specific activity of more than $2 \times 10^8$ IFU per mg protein.

68. The human leukocyte interferon of claim 67 having a specific activity of about $10^9$ IFU per mg protein.

69. The human leukocyte interferon of claim 67 having a specific activity of at least $10^9$ IFU per mg protein.

70. The human leukocyte interferon of claim 67 having a specific activity of $2 \times 10^9$ IFU per mg of protein.

71. Human lymphoblastoid interferon comprising a plurality of human leukocyte interferon species selected from the group of species having molecular weights of 18,410±200 daltons, 19,500±200 daltons, 20,180±200 daltons, 20,420±200 daltons, 21,130±200 daltons and 23,440±200 daltons, said molecular weights measured under non-reducing SDS-PAGE; and wherein said interferon has a specific activity of from about $2 \times 10^8$ to about $2 \times 10^9$ IFU per mg protein.

72. The human lymphoblastoid interferon of claim 71 having a specific activity of about $2 \times 10^8$ IFU per mg of protein.

73. The human lymphoblastoid interferon of claim 71 having a specific activity of about $10^9$ IFU per mg of protein.

74. The human lymphoblastoid interferon of claim 71 having a specific activity of $2 \times 10^9$ IFU per mg of protein.

75. The human lymphoblastoid interferon of claim 71 having a specific activity of from $2 \times 10^8$ to $2 \times 10^9$ IFU per mg of protein.

76. Human lymphoblastoid interferon comprising a plurality of human leukocyte interferon species selected from the group of species having molecular weights of 18,410±200 daltons, 19,500±200 daltons, 20,180±200 daltons, 20,420±200 daltons, 21,130±200 daltons and 23,440±200 daltons, said molecular weights measured under non-reducing SDS-PAGE; and wherein said interferon has a specific activity of at least $2 \times 10^8$ IFU per mg of protein.

77. The human lymphoblastoid interferon of claim 76 having a specific activity of at least $10^9$ IFU per mg protein.

78. Human lymphoblastoid interferon comprising a plurality of human leukocyte interferon species, each of said species corresponding to a species selected from the group of species having molecular weights of 18,410±200 daltons, 19,500±200 daltons, 20,180±200 daltons, 20,420±200 daltons, 21,130±200 daltons and 23,440±200 daltons, said molecular weights measured under non-reducing SDS-PAGE; and wherein said interferon has a specific activity of from about $2 \times 10^8$ to about $2 \times 10^9$ IFU per mg of protein.

79. The human lymphoblastoid interferon of claim 78 having a specific activity of about $2 \times 10^8$ IFU per mg of protein.

80. The human lymphoblastoid interferon of claim 78 having a specific activity of about $10^9$ IFU per mg of protein.

81. The human lymphoblastoid interferon of claim 78 having a specific activity of $2 \times 10^9$ IFU per mg of protein.

82. The human lymphoblastoid interferon of claim 78 having a specific activity of from $2 \times 10^8$ to $2 \times 10^9$ IFU per mg of protein.

83. Human lymphoblastoid interferon comprising a plurality of human leukocyte interferon species, each of said species corresponding to a species selected from the group of species having molecular weights of 18,410±200 daltons, 19,500±200 daltons, 20,180±200 daltons, 20,420±200 daltons, 21,130±200 daltons and 23,440±200 daltons, said molecular weights measured under non-reducing SDS-PAGE; and wherein said interferon has a specific activity of at least $2 \times 10^8$ IFU per mg of protein.

84. The human lymphoblastoid interferon of claim 83 having a specific activity of at least $10^9$ IFU per mg protein.

85. Namalva interferon comprising a plurality of human leukocyte interferon species selected from the group of species having molecular weights of 18,410±200 daltons, 19,500±200 daltons, 20,180±200 daltons, 20,420±200 daltons, 21,130±200 daltons and 23,440±200 daltons, said molecular weights measured under non-reducing SDS-PAGE; and wherein said interferon has a specific activity of from about $2 \times 10^8$ to about $2 \times 10^9$ IFU per mg of protein.

86. The Namalva interferon of claim 85 having a specific activity of about $2 \times 10^8$ IFU per mg of protein.

87. The Namalva interferon of claim 85 having a specific activity of about $10^9$ IFU per mg of protein.

88. The Namalva interferon of claim 85 having a specific activity of $2 \times 10^9$ IFU per mg of protein.

89. The Namalva interferon of claim 85 having a specific activity of from $2 \times 10^8$ to $2 \times 10^9$ IFU per mg of protein.

90. Namalva interferon comprising a plurality of human leukocyte interferon species selected from the group of species having molecular weights of 18,410±200 daltons, 19,500±200 daltons, 20,180±200 daltons, 20,420±200 daltons, 21,130±200 daltons and 23,440±200 daltons, said molecular weights measured under non-reducing SDS-PAGE; and wherein said interferon has a specific activity of at least $2 \times 10^8$ IFU per mg of protein.

91. The Namalva interferon of claim 90 having a specific activity of at least $10^9$ IFU per mg protein.

92. Namalva interferon comprising a plurality of human leukocyte interferon species, each of said species corresponding to a species selected from the group of species having molecular weights of 18,410±200 daltons, 19,500±200 daltons, 20,180±200 daltons, 20,420±200 daltons, 21,130±200 daltons and 23,440±200 daltons, said molecular weights measured under non-reducing SDS-PAGE; and wherein said interferon has a specific activity of from about $2 \times 10^8$ to about $2 \times 10^9$ IFU per mg of protein.

93. The Namalva interferon of claim 92 having a specific activity of about $2 \times 10^8$ IFU per mg of protein.

94. The Namalva interferon of claim 92 having a specific activity of about $10^9$ IFU per mg of protein.

95. The Namalva interferon of claim 92 having a specific activity of $2 \times 10^9$ IFU per mg of protein.

96. The Namalva interferon of claim 92 having a specific activity of from $2 \times 10^8$ to $2 \times 10^9$ IFU per mg of protein.

97. Namalva interferon comprising a plurality of human leukocyte interferon species, each of said species corresponding to a species selected from the group of species having molecular weights of 18,410±200 daltons, 19,500±200 daltons, 20,180±200 daltons, 20,420±200 daltons, 21,130±200 daltons and 23,440±200 daltons, said molecular weights measured under non-reducing SDS-PAGE; and wherein said interferon has a specific activity of at least $2 \times 10^8$ IFU per mg of protein.

98. The Namalva interferon of claim 97 having a specific activity of at least $10^9$ IFU per mg protein.

99. Namalva leukocyte interferon having a specific activity of about $2 \times 10^8$ IFU per mg of protein.

100. Namalva leukocyte interferon having a specific activity of about $10^9$ IFU per mg of protein.

101. Namalva leukocyte interferon having a specific activity of at least $2 \times 10^8$ IFU per mg of protein.

102. Namalva leukocyte interferon of claim 101 having a specific activity of at least $10^9$ IFU per mg of protein.

* * * * *

UNITED STATES PATENT AND TRADEMARK OFFICE
CERTIFICATE OF CORRECTION

PATENT NO. : 6,117,423

DATED : September 12, 2000

INVENTOR(S) : Berg

It is certified that error appears in the above-identified patent and that said Letters Patent is hereby corrected as shown below:

Page 1, Column 2, insert commas after Lerner, David and Littenberg.
Column 8, line 10, insert space after "1.".
Column 31, line 24, "(PIF) X" should read --$(PIF)^x$--.
Column 31, line 36, "X" should read --$^x$--.
Column 33, line 12, insert "IFU" after --$2x10^8$--

Signed and Sealed this

Fifteenth Day of May, 2001

*Attest:*

NICHOLAS P. GODICI

*Attesting Officer*     Acting Director of the United States Patent and Trademark Office